United States Patent
Tajik

(10) Patent No.: US 11,477,599 B2
(45) Date of Patent: Oct. 18, 2022

(54) DELAYED AUDIO FOLLOWING

(71) Applicant: Magic Leap, Inc., Plantation, FL (US)

(72) Inventor: Anastasia Andreyevna Tajik, Fort Lauderdale, FL (US)

(73) Assignee: Magic Leap, Inc., Plantation, FL (US)

( * ) Notice: Subject to any disclaimer, the term of this patent is extended or adjusted under 35 U.S.C. 154(b) by 0 days.

(21) Appl. No.: 17/175,269

(22) Filed: Feb. 12, 2021

(65) Prior Publication Data
US 2021/0258713 A1 Aug. 19, 2021

Related U.S. Application Data

(60) Provisional application No. 62/976,936, filed on Feb. 14, 2020.

(51) Int. Cl.
*H04S 7/00* (2006.01)
(52) U.S. Cl.
CPC .......... *H04S 7/304* (2013.01); *H04S 2400/01* (2013.01); *H04S 2400/11* (2013.01)
(58) Field of Classification Search
CPC ...... H04S 7/304; H04S 2400/01; H04R 1/028
USPC ............ 381/26, 74, 309, 310, 367, 370, 376
See application file for complete search history.

(56) References Cited

U.S. PATENT DOCUMENTS

2017/0195816 A1   7/2017  Shih et al.
2018/0091923 A1*  3/2018  Satongar ................ H04R 5/033

OTHER PUBLICATIONS

International Search Report and Written Opinion dated Apr. 27, 2021, for PCT Application No. PCT/US2021/17971, ten pages.

* cited by examiner

*Primary Examiner* — Yosef K Laekemariam
(74) *Attorney, Agent, or Firm* — Morrison & Foerster LLP

(57) ABSTRACT

Disclosed herein are systems and methods for presenting mixed reality audio. In an example method, audio is presented to a user of a wearable head device. A first position of the user's head at a first time is determined based on one or more sensors of the wearable head device. A second position of the user's head at a second time later than the first time is determined based on the one or more sensors. An audio signal is determined based on a difference between the first position and the second position. The audio signal is presented to the user via a speaker of the wearable head device. Determining the audio signal comprises determining an origin of the audio signal in a virtual environment. Presenting the audio signal to the user comprises presenting the audio signal as if originating from the determined origin. Determining the origin of the audio signal comprises applying an offset to a position of the user's head.

20 Claims, 11 Drawing Sheets

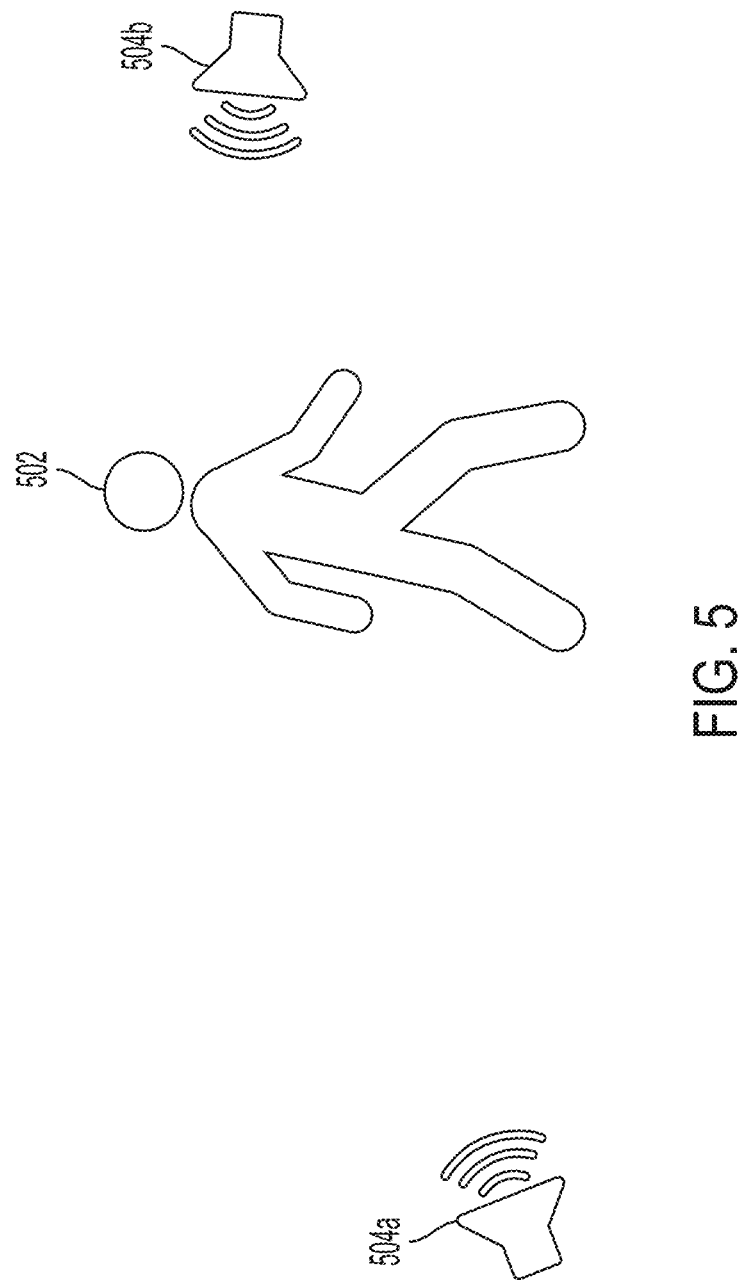

_US 11,477,599 B2_

DELAYED AUDIO FOLLOWING

CROSS-REFERENCE TO RELATED APPLICATIONS

This application claims benefit of U.S. Provisional Application No. 62/976,986, filed Feb. 14, 2020, the contents of which is incorporated herein by reference in its entirety.

FIELD

This disclosure relates in general to systems and methods for presenting audio to a user, and in particular to systems and methods for presenting audio to a user in a mixed reality environment.

BACKGROUND

Virtual environments are ubiquitous in computing environments, finding use in video games (in which a virtual environment may represent a game world); maps (in which a virtual environment may represent terrain to be navigated); simulations (in which a virtual environment may simulate a real environment); digital storytelling (in which virtual characters may interact with each other in a virtual environment); and many other applications. Modern computer users are generally comfortable perceiving, and interacting with, virtual environments. However, users' experiences with virtual environments can be limited by the technology for presenting virtual environments. For example, conventional displays (e.g., 2D display screens) and audio systems (e.g., fixed speakers) may be unable to realize a virtual environment in ways that create a compelling, realistic, and immersive experience.

Virtual reality ("VR"), augmented reality ("AR"), mixed reality ("MR"), and related technologies (collectively, "XR") share an ability to present, to a user of an XR system, sensory information corresponding to a virtual environment represented by data in a computer system. Such systems can offer a uniquely heightened sense of immersion and realism by combining virtual visual and audio cues with real sights and sounds. Accordingly, it can be desirable to present digital sounds to a user of an XR system in such a way that the sounds seem to be occurring—naturally, and consistently with the user's expectations of the sound—in the user's real environment. Generally speaking, users expect that virtual sounds will take on the acoustic properties of the real environment in which they are heard. For instance, a user of an XR system in a large concert hall will expect the virtual sounds of the XR system to have large, cavernous sonic qualities; conversely, a user in a small apartment will expect the sounds to be more dampened, close, and immediate. In addition to matching virtual sounds with acoustic properties of a real and/or virtual environment, realism is further enhanced by spatializing virtual sounds. For example, a virtual object may visually fly past a user from behind, and the user may expect the corresponding virtual sound to similarly reflect the spatial movement of the virtual object with respect to the user.

Existing technologies often fall short of these expectations, such as by presenting virtual audio that does not take into account a user's surroundings or does not correspond to spatial movements of a virtual object, leading to feelings of inauthenticity that can compromise the user experience. Observations of users of XR systems indicate that while users may be relatively forgiving of visual mismatches between virtual content and a real environment (e.g., inconsistencies in lighting); users may be more sensitive to auditory mismatches. Our own auditory experiences, refined continuously throughout our lives, can make us acutely aware of how our physical environments affect the sounds we hear; and we can be hyper-aware of sounds that are inconsistent with those expectations. With XR systems, such inconsistencies can be jarring, and can turn an immersive and compelling experience into a gimmicky, imitative one. In extreme examples, auditory inconsistencies can cause motion sickness and other ill effects as the inner ear is unable to reconcile auditory stimuli with their corresponding visual cues.

Because of our sensitivity to our audio senses, an immersive audio experience can be equally as important, if not more important, than an immersive visual experience. Because of the variety of sensing and computing power available to XR systems, XR systems may be positioned to offer much more immersive audio experiences than traditional audio systems, which may spatialize sound by splitting sound into one or more channels. For example, stereo headphones may present audio to a user using a left channel and a right channel to give the appearance of sound coming from different directions. Some stereo headphones may simulate additional channels (like 5.1 channels) to further enhance audio spatialization. However, traditional systems may suffer from the fact that the spatialized sound positions are static relative to the user. For example, a guitar sound that is presented to the user as originating five feet from the user's left ear may not dynamically change relative to the user as the user rotates their head. Such static behavior may not reflect audio behavior in a "real" environment. A person attending a live orchestra, for example, may experience slight changes in their audio experience based small head movements. These small acoustic behaviors may accumulate and add to an immersive audio experience. It is therefore desirable to develop audio systems and methods for XR systems to enhance a user's audio experience.

By taking into account the characteristics of the user's physical environment, the systems and methods described herein can simulate what would be heard by a user if the virtual sound were a real sound, generated naturally in that environment. By presenting virtual sounds in a manner that is faithful to the way sounds behave in the real world, the user may experience a heightened sense of connectedness to the mixed reality environment. Similarly, by presenting location-aware virtual content that responds to the user's movements and environment, the content becomes more subjective, interactive, and real—for example, the user's experience at Point A can be entirely different from his or her experience at Point B. This enhanced realism and interactivity can provide a foundation for new applications of mixed reality, such as those that use spatially-aware audio to enable novel forms of gameplay, social features, or interactive behaviors.

BRIEF SUMMARY

Examples of the disclosure describe systems and methods for presenting mixed reality audio. According to examples of the disclosure, audio is presented to a user of a wearable head device. A first position of the user's head at a first time is determined based on one or more sensors of the wearable head device. A second position of the user's head at a second time later than the first time is determined based on the one or more sensors. An audio signal is determined based on a difference between the first position and the second position. The audio signal is presented to the user via a speaker of the wearable head device. Determining the audio signal comprises determining an origin of the audio signal in a virtual environment. Presenting the audio signal to the user comprises presenting the audio signal as if originating from the determined origin. Determining the origin of the audio signal comprises applying an offset to a position of the user's head.

BRIEF DESCRIPTION OF THE DRAWINGS

FIG. 5 illustrates an example of mixed reality spatialized audio, according to some embodiments.

DETAILED DESCRIPTION

Figure 1A:
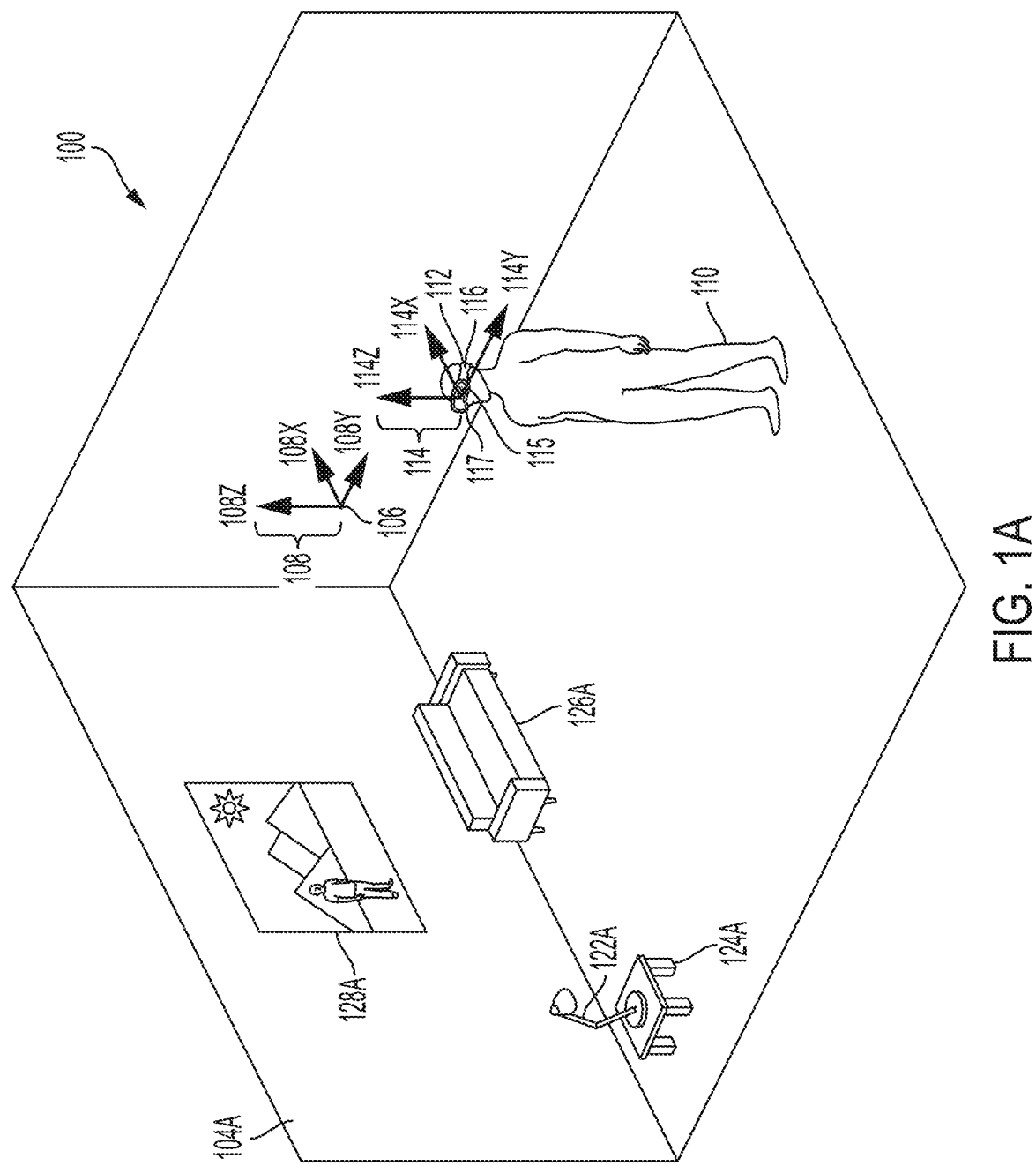
FIGS. 1A-1C illustrate an example mixed reality environment, according to some embodiments.

In the following description of examples, reference is made to the accompanying drawings which form a part hereof, and in which it is shown by way of illustration specific examples that can be practiced. It is to be understood that other examples can be used and structural changes can be made without departing from the scope of the disclosed examples.

Mixed Reality Environment

Like all people, a user of a mixed reality system exists in a real environment that is, a three-dimensional portion of the "real world," and all of its contents, that are perceptible by the user. For example, a user perceives a real environment using one's ordinary human senses—sight, sound, touch, taste, smell—and interacts with the real environment by moving one's own body in the real environment. Locations in a real environment can be described as coordinates in a coordinate space; for example, a coordinate can include latitude, longitude, and elevation with respect to sea level; distances in three orthogonal dimensions from a reference point; or other suitable values. Likewise, a vector can describe a quantity having a direction and a magnitude in the coordinate space.

A computing device can maintain, for example in a memory associated with the device, a representation of a virtual environment. As used herein, a virtual environment is a computational representation of a three-dimensional space. A virtual environment can include representations of any object, action, signal, parameter, coordinate, vector, or other characteristic associated with that space. In some examples, circuitry (e.g., a processor) of a computing device can maintain and update a state of a virtual environment; that is, a processor can determine at a first time t0, based on data associated with the virtual environment and/or input provided by a user, a state of the virtual environment at a second time t1. For instance, if an object in the virtual environment is located at a first coordinate at time t0, and has certain programmed physical parameters (e.g., mass, coefficient of friction); and an input received from user indicates that a force should be applied to the object in a direction vector; the processor can apply laws of kinematics to determine a location of the object at time t1 using basic mechanics. The processor can use any suitable information known about the virtual environment, and/or any suitable input, to determine a state of the virtual environment at a time t1. In maintaining and updating a state of a virtual environment, the processor can execute any suitable software, including software relating to the creation and deletion of virtual objects in the virtual environment; software (e.g., scripts) for defining behavior of virtual objects or characters in the virtual environment; software for defining the behavior of signals (e.g., audio signals) in the virtual environment; software for creating and updating parameters associated with the virtual environment; software for generating audio signals in the virtual environment; software for handling input and output; software for implementing network operations; software for applying asset data (e.g., animation data to move a virtual object over time); or many other possibilities.

Output devices, such as a display or a speaker, can present any or all aspects of a virtual environment to a user. For example, a virtual environment may include virtual objects (which may include representations of inanimate objects; people; animals; lights; etc.) that may be presented to a user. A processor can determine a view of the virtual environment (for example, corresponding to a "camera" with an origin coordinate, a view axis, and a frustum); and render, to a display, a viewable scene of the virtual environment corresponding to that view. Any suitable rendering technology may be used for this purpose. In some examples, the viewable scene may include only some virtual objects in the virtual environment, and exclude certain other virtual objects. Similarly, a virtual environment may include audio aspects that may be presented to a user as one or more audio signals. For instance, a virtual object in the virtual environment may generate a sound originating from a location coordinate of the object (e.g., a virtual character may speak or cause a sound effect); or the virtual environment may be associated with musical cues or ambient sounds that may or may not be associated with a particular location. A processor can determine an audio signal corresponding to a "listener" coordinate—for instance, an audio signal corresponding to a composite of sounds in the virtual environment, and mixed and processed to simulate an audio signal that would be heard by a listener at the listener coordinate—and present the audio signal to a user via one or more speakers.

Because a virtual environment exists only as a computational structure, a user cannot directly perceive a virtual environment using one's ordinary senses. Instead, a user can perceive a virtual environment only indirectly, as presented to the user, for example by a display, speakers, haptic output devices, etc. Similarly, a user cannot directly touch, manipulate, or otherwise interact with a virtual environment; but can provide input data, via input devices or sensors, to a processor that can use the device or sensor data to update the virtual environment. For example, a camera sensor can provide optical data indicating that a user is trying to move an object in a virtual environment, and a processor can use that data to cause the object to respond accordingly in the virtual environment.

A mixed reality system can present to the user, for example using a transmissive display and/or one or more speakers (which may, for example, be incorporated into a wearable head device), a mixed reality environment ("MRE") that combines aspects of a real environment and a virtual environment. In some embodiments, the one or more speakers may be external to the head-mounted wearable unit. As used herein, a MRE is a simultaneous representation of a real environment and a corresponding virtual environment. In some examples, the corresponding real and virtual environments share a single coordinate space; in some examples, a real coordinate space and a corresponding virtual coordinate space are related to each other by a transformation matrix (or other suitable representation). Accordingly, a single coordinate (along with, in some examples, a transformation matrix) can define a first location in the real environment, and also a second, corresponding, location in the virtual environment; and vice versa.

In a MRE, a virtual object (e.g., in a virtual environment associated with the MRE) can correspond to a real object (e.g., in a real environment associated with the MRE). For instance, if the real environment of a MRE includes a real lamp post (a real object) at a location coordinate, the virtual environment of the MRE may include a virtual lamp post (a virtual object) at a corresponding location coordinate. As used herein, the real object in combination with its corresponding virtual object together constitute a "mixed reality object." It is not necessary for a virtual object to perfectly match or align with a corresponding real object. In some examples, a virtual object can be a simplified version of a corresponding real object. For instance, if a real environment includes a real lamp post, a corresponding virtual object may include a cylinder of roughly the same height and radius as the real lamp post (reflecting that lamp posts may be roughly cylindrical in shape). Simplifying virtual objects in this manner can allow computational efficiencies, and can simplify calculations to be performed on such virtual objects. Further, in some examples of a MRE, not all real objects in a real environment may be associated with a corresponding virtual object. Likewise, in some examples of a MRE, not all virtual objects in a virtual environment may be associated with a corresponding real object. That is, some virtual objects may solely in a virtual environment of a MRE, without any real-world counterpart.

In some examples, virtual objects may have characteristics that differ, sometimes drastically, from those of corresponding real objects. For instance, while a real environment in a MRE may include a green, two-armed cactus—a prickly inanimate object—a corresponding virtual object in the MRE may have the characteristics of a green, two-armed virtual character with human facial features and a surly demeanor. In this example, the virtual object resembles its corresponding real object in certain characteristics (color, number of arms); but differs from the real object in other characteristics (facial features, personality). In this way, virtual objects have the potential to represent real objects in a creative, abstract, exaggerated, or fanciful manner; or to impart behaviors (e.g., human personalities) to otherwise inanimate real objects. In some examples, virtual objects may be purely fanciful creations with no real-world counterpart (e.g., a virtual monster in a virtual environment, perhaps at a location corresponding to an empty space in a real environment).

Compared to VR systems, which present the user with a virtual environment while obscuring the real environment, a mixed reality system presenting a MRE affords the advantage that the real environment remains perceptible while the virtual environment is presented. Accordingly, the user of the mixed reality system is able to use visual and audio cues associated with the real environment to experience and interact with the corresponding virtual environment. As an example, while a user of VR systems may struggle to perceive or interact with a virtual object displayed in a virtual environment—because, as noted above, a user cannot directly perceive or interact with a virtual environment—a user of a MR system may find it intuitive and natural to interact with a virtual object by seeing, hearing, and touching a corresponding real object in his or her own real environment. This level of interactivity can heighten a user's feelings of immersion, connection, and engagement with a virtual environment. Similarly, by simultaneously presenting a real environment and a virtual environment, mixed reality systems can reduce negative psychological feelings (e.g., cognitive dissonance) and negative physical feelings (e.g., motion sickness) associated with VR systems. Mixed reality systems further offer many possibilities for applications that may augment or alter our experiences of the real world.

FIG. 1A illustrates an example real environment 100 in which a user 110 uses a mixed reality system 112. Mixed reality system 112 may include a display (e.g., a transmissive display) and one or more speakers, and one or more sensors (e.g., a camera), for example as described below. The real environment 100 shown includes a rectangular room 104A, in which user 110 is standing; and real objects 122A (a lamp), 124A (a table), 126A (a sofa), and 128A (a painting). Room 104A further includes a location coordinate 106, which may be considered an origin of the real environment 100. As shown in FIG. 1A, an environment/world coordinate system 108 (comprising an x-axis 108X, a y-axis 108Y, and a z-axis 108Z) with its origin at point 106 (a world coordinate), can define a coordinate space for real environment 100. In some embodiments, the origin point 106 of the environment/world coordinate system 108 may correspond to where the mixed reality system 112 was powered on. In some embodiments, the origin point 106 of the environment/world coordinate system 108 may be reset during operation. In some examples, user 110 may be considered a real object in real environment 100; similarly, user 110's body parts (e.g., hands, feet) may be considered real objects in real environment 100. In some examples, a user/listener/head coordinate system 114 (comprising an x-axis 114X, a y-axis 114Y, and a z-axis 114Z) with its origin at point 115 (e.g., user/listener/head coordinate) can define a coordinate space for the user/listener/head on which the mixed reality system 112 is located. The origin point 115 of the user/listener/head coordinate system 114 may be defined relative to one or more components of the mixed reality system 112. For example, the origin point 115 of the user/listener/head coordinate system 114 may be defined relative to the display of the mixed reality system 112 such as during initial calibration of the mixed reality system 112. A matrix (which may include a translation matrix and a Quaternion matrix or other rotation matrix), or other suitable representation can characterize a transformation between the user/listener/head coordinate system 114 space and the environment/world coordinate system 108 space. In some embodiments, a left ear coordinate 116 and a right ear coordinate 117 may be defined relative to the origin point 115 of the user/listener/head coordinate system 114. A matrix (which may include a translation matrix and a Quaternion matrix or other rotation matrix), or other suitable representation can characterize a transformation between the left ear coordinate 116 and the right ear coordinate 117, and user/listener/head coordinate system 114 space. The user/listener/head coordinate system 114 can simplify the representation of locations relative to the user's head, or to a head-mounted device, for example, relative to the environment/world coordinate system 108.

Using Simultaneous Localization and Mapping (SLAM), visual odometry, or other techniques, a transformation between user coordinate system 114 and environment coordinate system 108 can be determined and updated in real-time.

Figure 1B:
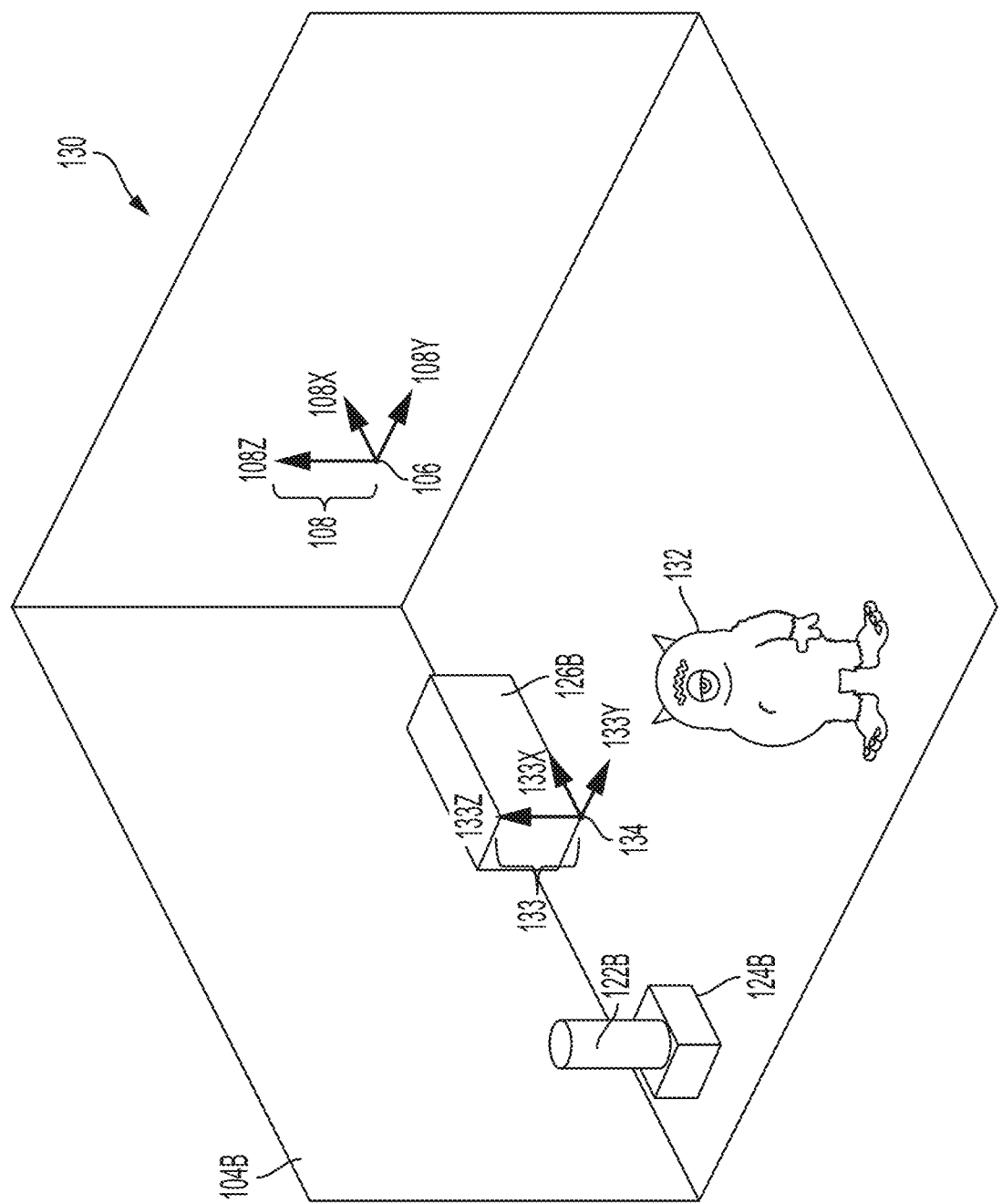

FIG. 1B illustrates an example virtual environment 130 that corresponds to real environment 100. The virtual environment 130 shown includes a virtual rectangular room 104B corresponding to real rectangular room 104A; a virtual object 122B corresponding to real object 122A; a virtual object 124B corresponding to real object 124A; and a virtual object 126B corresponding to real object 126A. Metadata associated with the virtual objects 122B, 124B, 126B can include information derived from the corresponding real objects 122A, 124A, 126A. Virtual environment 130 additionally includes a virtual monster 132, which does not correspond to any real object in real environment 100. Real object 128A in real environment 100 does not correspond to any virtual object in virtual environment 130. A persistent coordinate system 133 (comprising an x-axis 133X, a y-axis 133Y, and a z-axis 133Z) with its origin at point 134 (persistent coordinate), can define a coordinate space for virtual content. The origin point 134 of the persistent coordinate system 133 may be defined relative/with respect to one or more real objects, such as the real object 126A. A matrix (which may include a translation matrix and a Quaternion matrix or other rotation matrix), or other suitable representation can characterize a transformation between the persistent coordinate system 133 space and the environment/world coordinate system 108 space. In some embodiments, each of the virtual objects 122B, 124B, 126B, and 132 may have their own persistent coordinate point relative to the origin point 134 of the persistent coordinate system 133. In some embodiments, there may be multiple persistent coordinate systems and each of the virtual objects 122B, 124B, 126B, and 132 may have their own persistent coordinate point relative to one or more persistent coordinate systems.

With respect to FIGS. 1A and 1B, environment/world coordinate system 108 defines a shared coordinate space for both real environment 100 and virtual environment 130. In the example shown, the coordinate space has its origin at point 106. Further, the coordinate space is defined by the same three orthogonal axes (108X, 108Y, 108Z). Accordingly, a first location in real environment 100, and a second, corresponding location in virtual environment 130, can be described with respect to the same coordinate space. This simplifies identifying and displaying corresponding locations in real and virtual environments, because the same coordinates can be used to identify both locations. However, in some examples, corresponding real and virtual environments need not use a shared coordinate space. For instance, in some examples (not shown), a matrix (which may include a translation matrix and a Quaternion matrix or other rotation matrix), or other suitable representation can characterize a transformation between a real environment coordinate space and a virtual environment coordinate space.

Figure 1C:
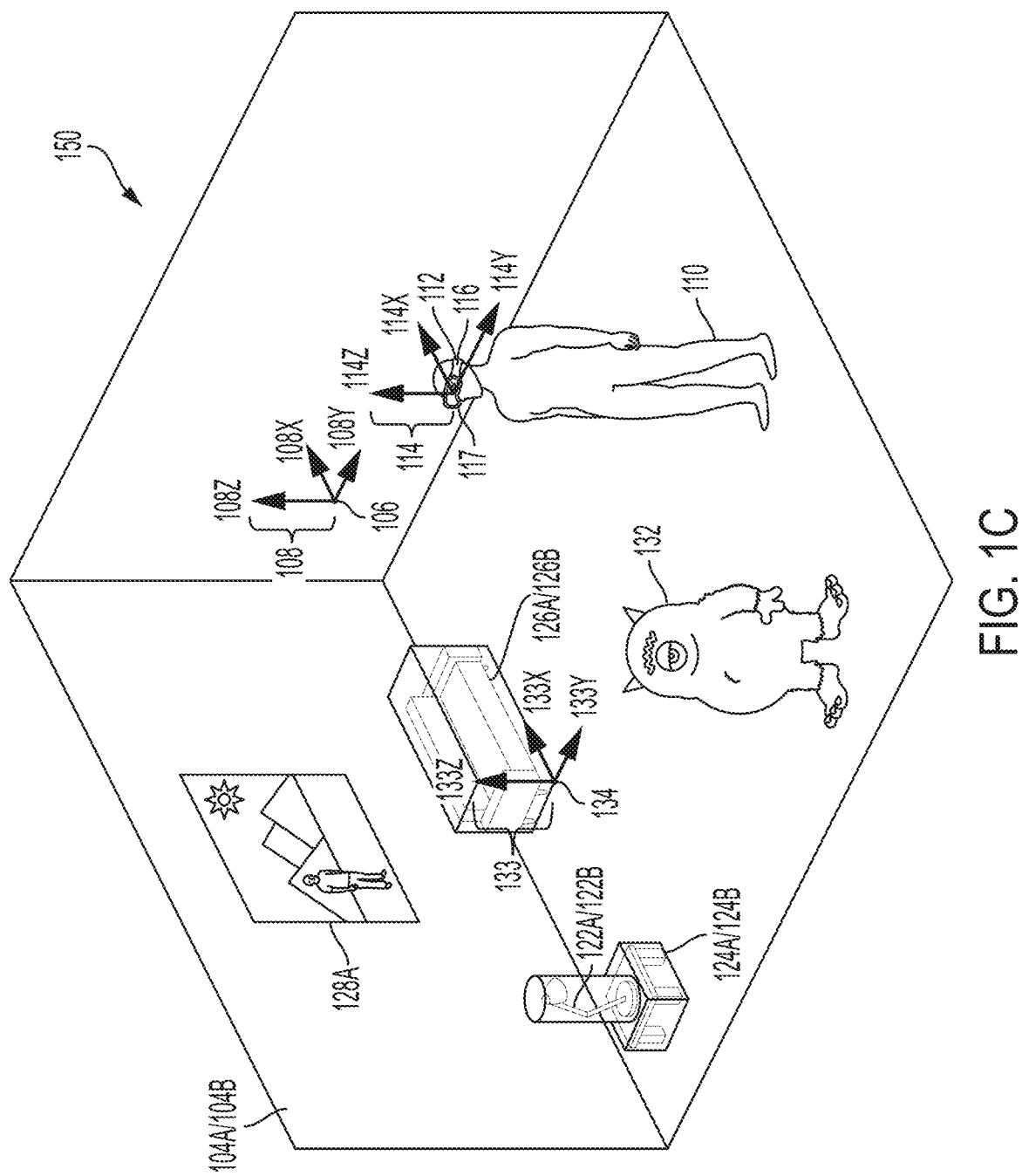

FIG. 1C illustrates an example MRE 150 that simultaneously presents aspects of real environment 100 and virtual environment 130 to user 110 via mixed reality system 112. In the example shown, MRE 150 simultaneously presents user 110 with real objects 122A, 124A, 126A, and 128A from real environment 100 (e.g., via a transmissive portion of a display of mixed reality system 112); and virtual objects 122B, 124B, 126B, and 132 from virtual environment 130 (e.g., via an active display portion of the display of mixed reality system 112). As above, origin point 106 acts as an origin for a coordinate space corresponding to MRE 150, and coordinate system 108 defines an x-axis, y-axis, and z-axis for the coordinate space.

In the example shown, mixed reality objects include corresponding pairs of real objects and virtual objects (i.e., 122A/122B, 124A/124B, 126A/126B) that occupy corresponding locations in coordinate space 108. In some examples, both the real objects and the virtual objects may be simultaneously visible to user 110. This may be desirable in, for example, instances where the virtual object presents information designed to augment a view of the corresponding real object (such as in a museum application where a virtual object presents the missing pieces of an ancient damaged sculpture). In some examples, the virtual objects (122B, 124B, and/or 126B) may be displayed (e.g., via active pixelated occlusion using a pixelated occlusion shutter) so as to occlude the corresponding real objects (122A, 124A, and/or 126A). This may be desirable in, for example, instances where the virtual object acts as a visual replacement for the corresponding real object (such as in an interactive storytelling application where an inanimate real object becomes a "living" character).

In some examples, real objects (e.g., 122A, 124A, 126A) may be associated with virtual content or helper data that may not necessarily constitute virtual objects. Virtual content or helper data can facilitate processing or handling of virtual objects in the mixed reality environment. For example, such virtual content could include two-dimensional representations of corresponding real objects; custom asset types associated with corresponding real objects; or statistical data associated with corresponding real objects. This information can enable or facilitate calculations involving a real object without incurring unnecessary computational overhead.

In some examples, the presentation described above may also incorporate audio aspects. For instance, in MRE 150, virtual monster 132 could be associated with one or more audio signals, such as a footstep sound effect that is generated as the monster walks around MRE 150. As described further below, a processor of mixed reality system 112 can compute an audio signal corresponding to a mixed and processed composite of all such sounds in MRE 150, and present the audio signal to user 110 via one or more speakers included in mixed reality system 112 and/or one or more external speakers.

Example Mixed Reality System

Example mixed reality system 112 can include a wearable head device (e.g., a wearable augmented reality or mixed reality head device) comprising a display (which may include left and right transmissive displays, which may be near-eye displays, and associated components for coupling light from the displays to the user's eyes); left and right speakers (e.g., positioned adjacent to the user's left and right ears, respectively); an inertial measurement unit (IMU)(e.g., mounted to a temple arm of the head device); an orthogonal coil electromagnetic receiver (e.g., mounted to the left temple piece); left and right cameras (e.g., depth (time-of-flight) cameras) oriented away from the user; and left and right eye cameras oriented toward the user (e.g., for detecting the user's eye movements). However, a mixed reality system 112 can incorporate any suitable display technology, and any suitable sensors (e.g., optical, infrared, acoustic, LIDAR, EOG, GPS, magnetic). In addition, mixed reality system 112 may incorporate networking features (e.g., Wi-Fi capability) to communicate with other devices and systems, including other mixed reality systems. Mixed reality system 112 may further include a battery (which may be mounted in an auxiliary unit, such as a belt pack designed to be worn around a user's waist), a processor, and a memory. The wearable head device of mixed reality system 112 may include tracking components, such as an IMU or other suitable sensors, configured to output a set of coordinates of the wearable head device relative to the user's environment. In some examples, tracking components may provide input to a processor performing a Simultaneous Localization and Mapping (SLAM) and/or visual odometry algorithm. In some examples, mixed reality system 112 may also include a handheld controller 300, and/or an auxiliary unit 320, which may be a wearable beltpack, as described further below.

Figure 2A:
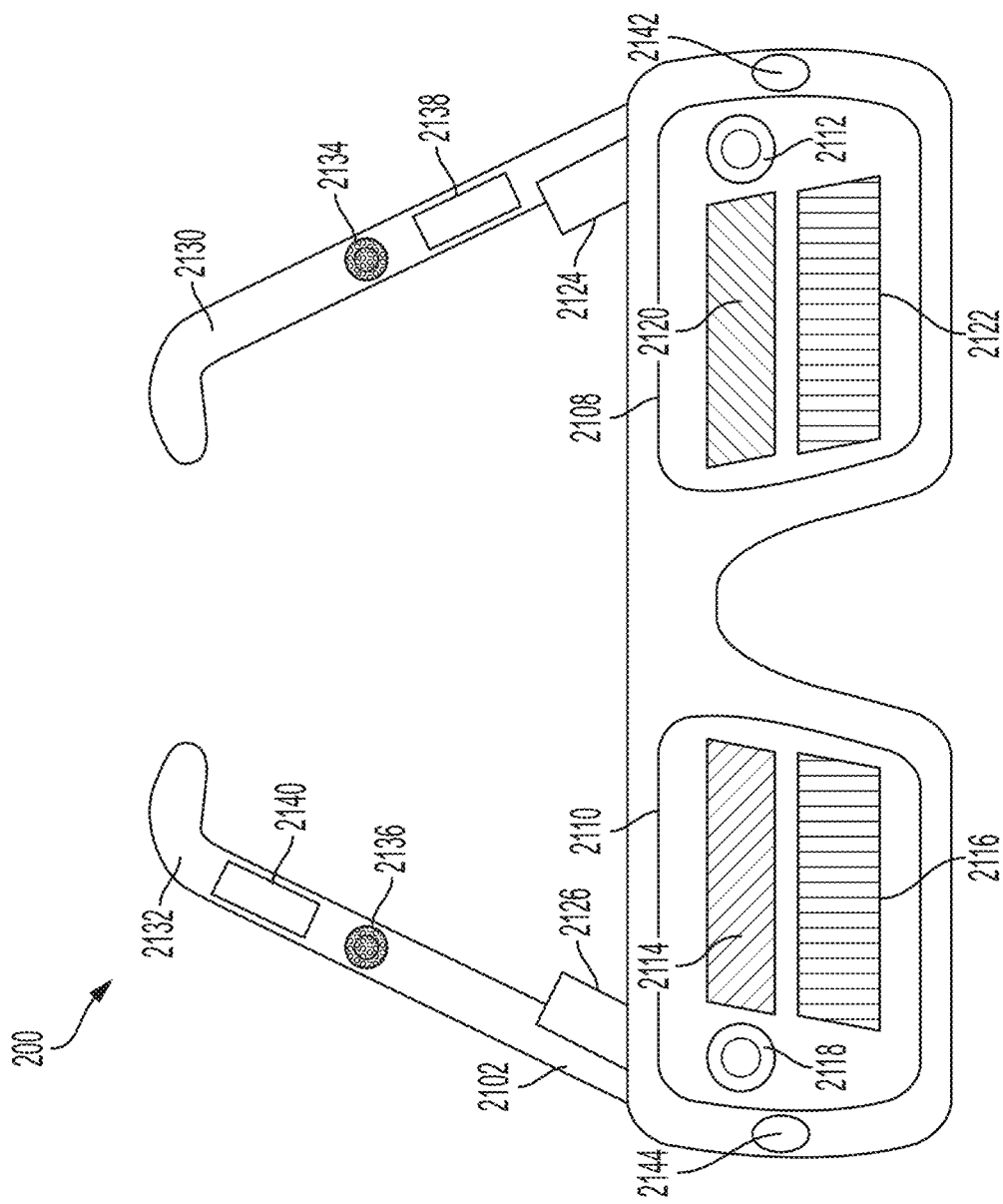
FIGS. 2A-2D illustrate components of an example mixed reality system that can be used to generate and interact with a mixed reality environment, according to some embodiments.
Figure 2B:
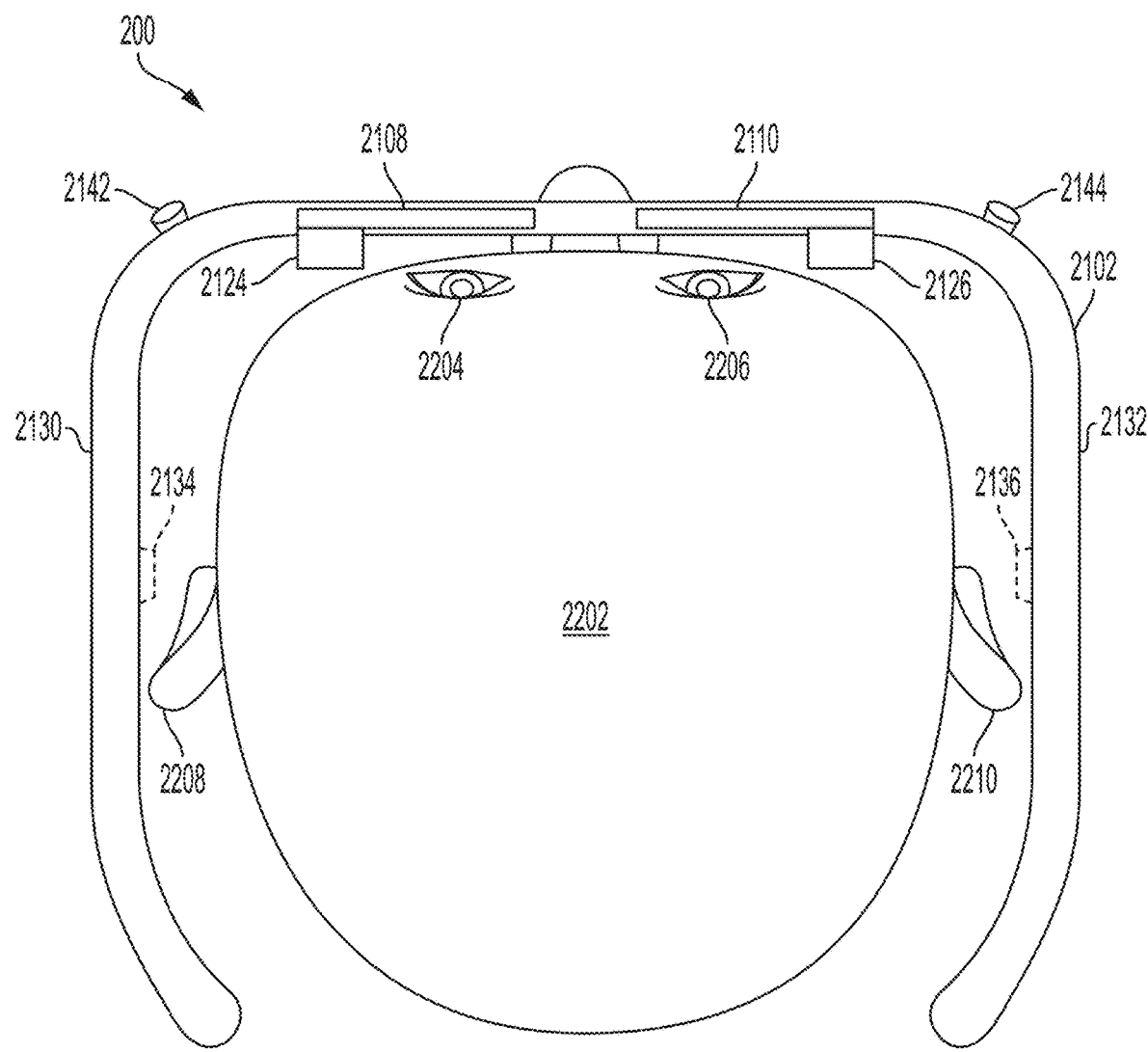
Figure 2C:
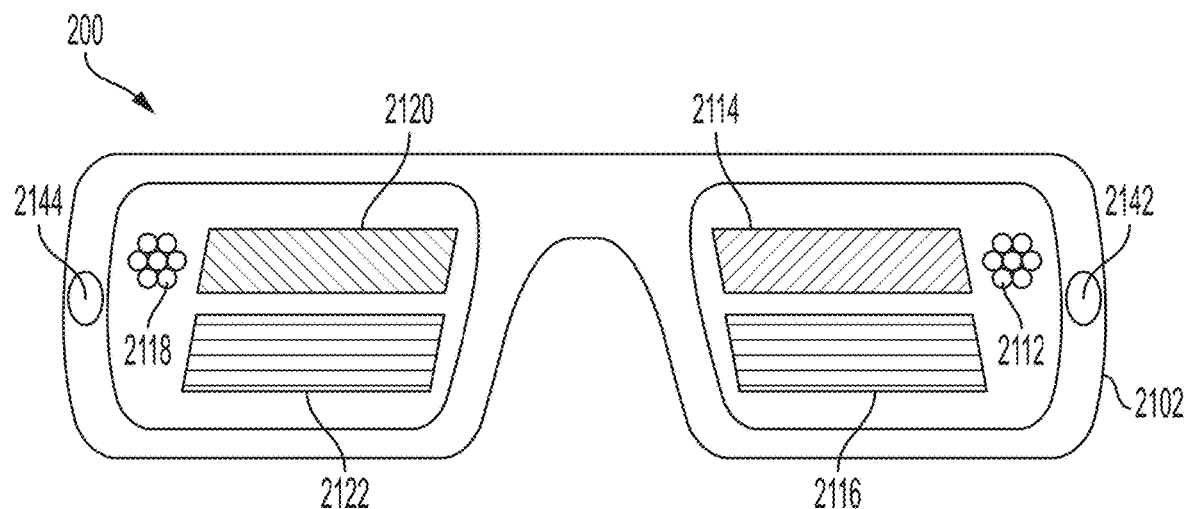
Figure 2D:
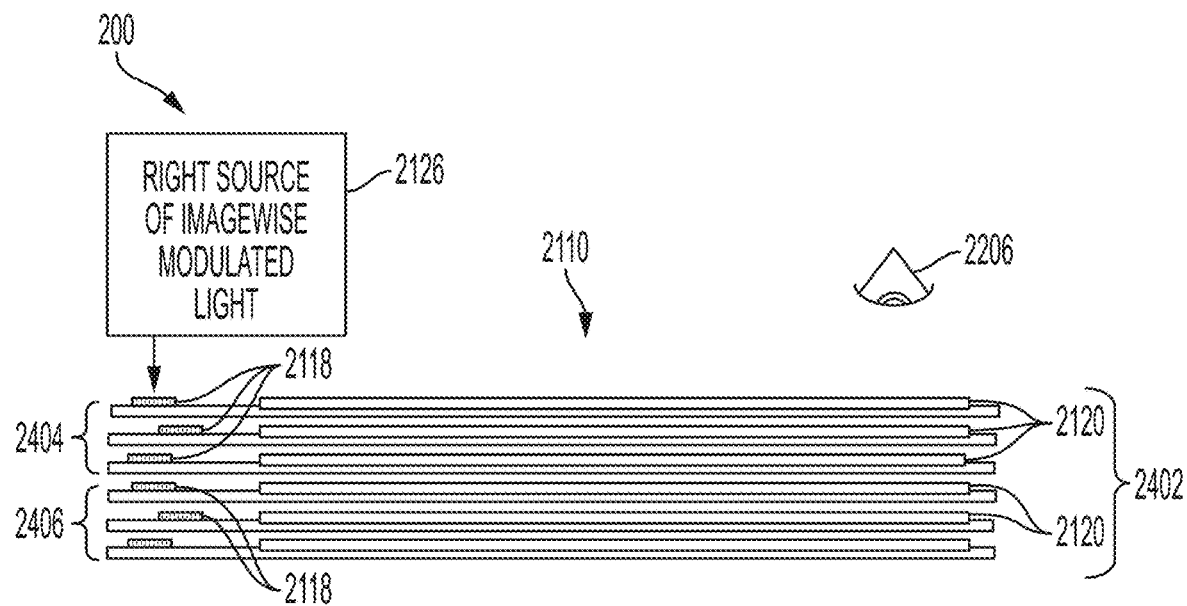

FIGS. 2A-2D illustrate components of an example mixed reality system 200 (which may correspond to mixed reality system 112) that may be used to present a MRE (which may correspond to MRE 150), or other virtual environment, to a user. FIG. 2A illustrates a perspective view of a wearable head device 2102 included in example mixed reality system 200. FIG. 2B illustrates a top view of wearable head device 2102 worn on a user's head 2202. FIG. 2C illustrates a front view of wearable head device 2102. FIG. 2D illustrates an edge view of example eyepiece 2110 of wearable head device 2102. As shown in FIGS. 2A-2C, the example wearable head device 2102 includes an example left eyepiece (e.g., a left transparent waveguide set eyepiece) 2108 and an example right eyepiece (e.g., a right transparent waveguide set eyepiece) 2110. Each eyepiece 2108 and 2110 can include transmissive elements through which a real environment can be visible, as well as display elements for presenting a display (e.g., via imagewise modulated light) overlapping the real environment. In some examples, such display elements can include surface diffractive optical elements for controlling the flow of imagewise modulated light. For instance, the left eyepiece 2108 can include a left incoupling grating set 2112, a left orthogonal pupil expansion (OPE) grating set 2120, and a left exit (output) pupil expansion (EPE) grating set 2122. Similarly, the right eyepiece 2110 can include a right incoupling grating set 2118, a right OPE grating set 2114 and a right EPE grating set 2116. Imagewise modulated light can be transferred to a user's eye via the incoupling gratings 2112 and 2118, OPEs 2114 and 2120, and EPE 2116 and 2122. Each incoupling grating set 2112, 2118 can be configured to deflect light toward its corresponding OPE grating set 2120, 2114. Each OPE grating set 2120, 2114 can be designed to incrementally deflect light down toward its associated EPE 2122, 2116, thereby horizontally extending an exit pupil being formed. Each EPE 2122, 2116 can be configured to incrementally redirect at least a portion of light received from its corresponding OPE grating set 2120, 2114 outward to a user eyebox position (not shown) defined behind the eyepieces 2108, 2110, vertically extending the exit pupil that is formed at the eyebox. Alternatively, in lieu of the incoupling grating sets 2112 and 2118, OPE grating sets 2114 and 2120, and EPE grating sets 2116 and 2122, the eyepieces 2108 and 2110 can include other arrangements of gratings and/or refractive and reflective features for controlling the coupling of imagewise modulated light to the user's eyes.

In some examples, wearable head device 2102 can include a left temple arm 2130 and a right temple arm 2132, where the left temple arm 2130 includes a left speaker 2134 and the right temple arm 2132 includes a right speaker 2136. An orthogonal coil electromagnetic receiver 2138 can be located in the left temple piece, or in another suitable location in the wearable head unit 2102. An Inertial Measurement Unit (IMU) 2140 can be located in the right temple arm 2132, or in another suitable location in the wearable head device 2102. The wearable head device 2102 can also include a left depth (e.g., time-of-flight) camera 2142 and a right depth camera 2144. The depth cameras 2142, 2144 can be suitably oriented in different directions so as to together cover a wider field of view.

In the example shown in FIGS. 2A-2D, a left source of imagewise modulated light 2124 can be optically coupled into the left eyepiece 2108 through the left incoupling grating set 2112, and a right source of imagewise modulated light 2126 can be optically coupled into the right eyepiece 2110 through the right incoupling grating set 2118. Sources of imagewise modulated light 2124, 2126 can include, for example, optical fiber scanners; projectors including electronic light modulators such as Digital Light Processing (DLP) chips or Liquid Crystal on Silicon (LCoS) modulators; or emissive displays, such as micro Light Emitting Diode (µLED) or micro Organic Light Emitting Diode (µOLED) panels coupled into the incoupling grating sets 2112, 2118 using one or more lenses per side. The input coupling grating sets 2112, 2118 can deflect light from the sources of imagewise modulated light 2124, 2126 to angles above the critical angle for Total Internal Reflection (TIR) for the eyepieces 2108, 2110. The OPE grating sets 2114, 2120 incrementally deflect light propagating by TIR down toward the EPE grating sets 2116, 2122. The EPE grating sets 2116, 2122 incrementally couple light toward the user's face, including the pupils of the user's eyes.

In some examples, as shown in FIG. 2D, each of the left eyepiece 2108 and the right eyepiece 2110 includes a plurality of waveguides 2402. For example, each eyepiece 2108, 2110 can include multiple individual waveguides, each dedicated to a respective color channel (e.g., red, blue and green). In some examples, each eyepiece 2108, 2110 can include multiple sets of such waveguides, with each set configured to impart different wavefront curvature to emitted light. The wavefront curvature may be convex with respect to the user's eyes, for example to present a virtual object positioned a distance in front of the user (e.g., by a distance corresponding to the reciprocal of wavefront curvature). In some examples, EPE grating sets 2116, 2122 can include curved grating grooves to effect convex wavefront curvature by altering the Poynting vector of exiting light across each EPE.

In some examples, to create a perception that displayed content is three-dimensional, stereoscopically-adjusted left and right eye imagery can be presented to the user through the imagewise light modulators 2124, 2126 and the eyepieces 2108, 2110. The perceived realism of a presentation of a three-dimensional virtual object can be enhanced by selecting waveguides (and thus corresponding the wavefront curvatures) such that the virtual object is displayed at a distance approximating a distance indicated by the stereoscopic left and right images. This technique may also reduce motion sickness experienced by some users, which may be caused by differences between the depth perception cues provided by stereoscopic left and right eye imagery, and the autonomic accommodation (e.g., object distance-dependent focus) of the human eye.

FIG. 2D illustrates an edge-facing view from the top of the right eyepiece 2110 of example wearable head device 2102. As shown in FIG. 2D, the plurality of waveguides 2402 can include a first subset of three waveguides 2404 and a second subset of three waveguides 2406. The two subsets of waveguides 2404, 2406 can be differentiated by different EPE gratings featuring different grating line curvatures to impart different wavefront curvatures to exiting light. Within each of the subsets of waveguides 2404, 2406 each waveguide can be used to couple a different spectral channel (e.g., one of red, green and blue spectral channels) to the user's right eye 2206. (Although not shown in FIG. 2D, the structure of the left eyepiece 2108 is analogous to the structure of the right eyepiece 2110.)

Figure 3A:
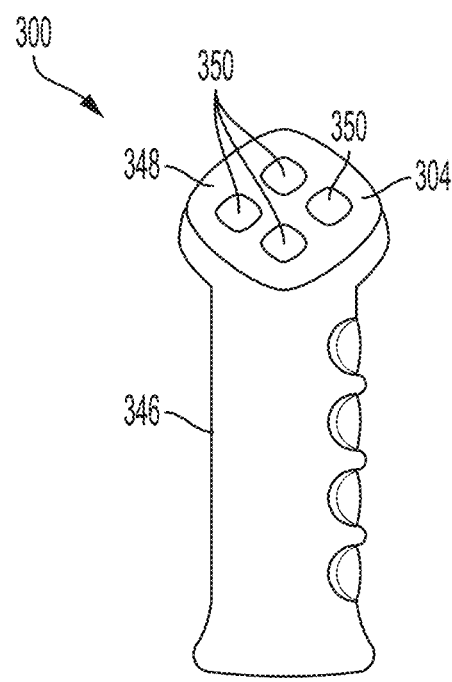
FIG. 3A illustrates an example mixed reality handheld controller that can be used to provide input to a mixed reality environment, according to some embodiments.

FIG. 3A illustrates an example handheld controller component 300 of a mixed reality system 200. In some examples, handheld controller 300 includes a grip portion 346 and one or more buttons 350 disposed along a top surface 348. In some examples, buttons 350 may be configured for use as an optical tracking target, e.g., for tracking six-degree-of-freedom (6DOF) motion of the handheld controller 300, in conjunction with a camera or other optical sensor (which may be mounted in a head unit (e.g., wearable head device 2102) of mixed reality system 200). In some examples, handheld controller 300 includes tracking components (e.g., an IMU or other suitable sensors) for detecting position or orientation, such as position or orientation relative to wearable head device 2102. In some examples, such tracking components may be positioned in a handle of handheld controller 300, and/or may be mechanically coupled to the handheld controller. Handheld controller 300 can be configured to provide one or more output signals corresponding to one or more of a pressed state of the buttons; or a position, orientation, and/or motion of the handheld controller 300 (e.g., via an IMU). Such output signals may be used as input to a processor of mixed reality system 200. Such input may correspond to a position, orientation, and/or movement of the handheld controller (and, by extension, to a position, orientation, and/or movement of a hand of a user holding the controller). Such input may also correspond to a user pressing buttons 350.

Figure 3B:
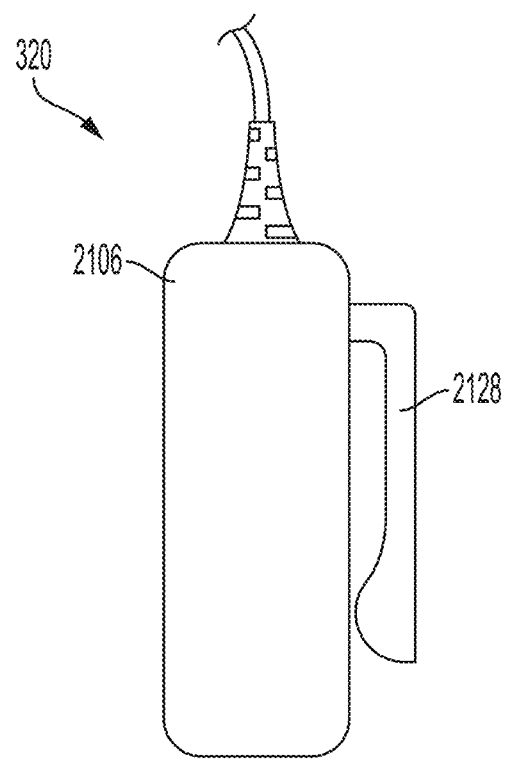
FIG. 3B illustrates an example auxiliary unit that can be used with an example mixed reality system, according to some embodiments.

FIG. 3B illustrates an example auxiliary unit 320 of a mixed reality system 200. The auxiliary unit 320 can include a battery to provide energy to operate the system 200, and can include a processor for executing programs to operate the system 200. As shown, the example auxiliary unit 320 includes a clip 2128, such as for attaching the auxiliary unit 320 to a user's belt. Other form factors are suitable for auxiliary unit 320 and will be apparent, including form factors that do not involve mounting the unit to a user's belt. In some examples, auxiliary unit 320 is coupled to the wearable head device 2102 through a multiconduit cable that can include, for example, electrical wires and fiber optics. Wireless connections between the auxiliary unit 320 and the wearable head device 2102 can also be used.

In some examples, mixed reality system 200 can include one or more microphones to detect sound and provide corresponding signals to the mixed reality system. In some examples, a microphone may be attached to, or integrated with, wearable head device 2102, and may be configured to detect a user's voice. In some examples, a microphone may be attached to, or integrated with, handheld controller 300 and/or auxiliary unit 320. Such a microphone may be configured to detect environmental sounds, ambient noise, voices of a user or a third party, or other sounds.

Figure 4:
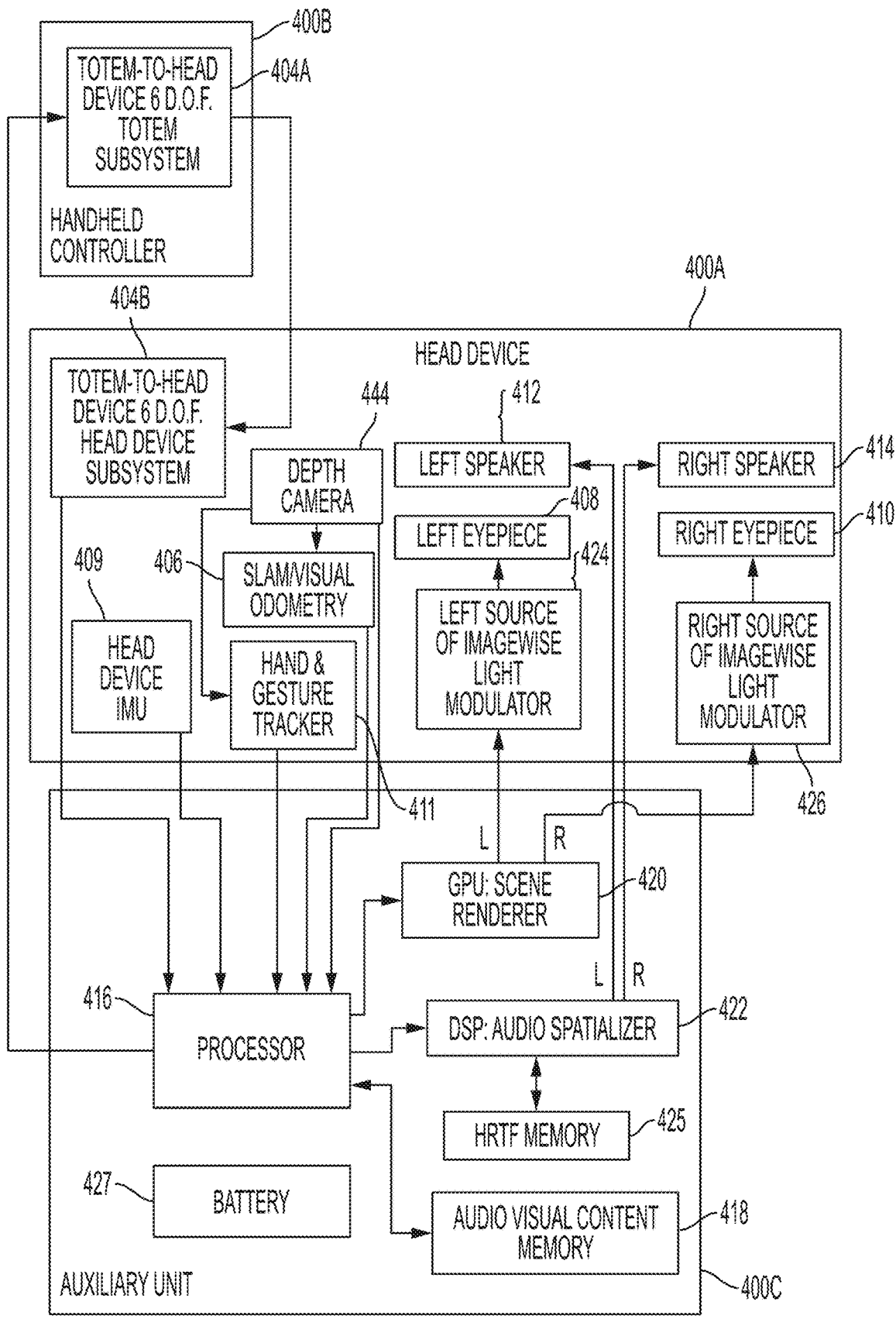
FIG. 4 illustrates an example functional block diagram for an example mixed reality system, according to some embodiments.

FIG. 4 shows an example functional block diagram that may correspond to an example mixed reality system, such as mixed reality system 200 described above (which may correspond to mixed reality system 112 with respect to FIG. 1). As shown in FIG. 4, example handheld controller 400B (which may correspond to handheld controller 300 (a "totem")) includes a totem-to-wearable head device six degree of freedom (6DOF) totem subsystem 404A and example wearable head device 400A (which may correspond to wearable head device 2102) includes a totem-to-wearable head device 6DOF subsystem 404B. In the example, the 6DOF totem subsystem 404A and the 6DOF subsystem 404B cooperate to determine six coordinates (e.g., offsets in three translation directions and rotation along three axes) of the handheld controller 400B relative to the wearable head device 400A. The six degrees of freedom may be expressed relative to a coordinate system of the wearable head device 400A. The three translation offsets may be expressed as X, Y, and Z offsets in such a coordinate system, as a translation matrix, or as some other representation. The rotation degrees of freedom may be expressed as sequence of yaw, pitch and roll rotations, as a rotation matrix, as a quaternion, or as some other representation. In some examples, the wearable head device 400A; one or more depth cameras 444 (and/or one or more non-depth cameras) included in the wearable head device 400A; and/or one or more optical targets (e.g., buttons 350 of handheld controller 400B as described above, or dedicated optical targets included in the handheld controller 400B) can be used for 6DOF tracking. In some examples, the handheld controller 400B can include a camera, as described above; and the wearable head device 400A can include an optical target for optical tracking in conjunction with the camera. In some examples, the wearable head device 400A and the handheld controller 400B each include a set of three orthogonally oriented solenoids which are used to wirelessly send and receive three distinguishable signals. By measuring the relative magnitude of the three distinguishable signals received in each of the coils used for receiving, the 6DOF of the wearable head device 400A relative to the handheld controller 400B may be determined. Additionally, 6DOF totem subsystem 404A can include an Inertial Measurement Unit (IMU) that is useful to provide improved accuracy and/or more timely information on rapid movements of the handheld controller 400B.

In some examples, it may become necessary to transform coordinates from a local coordinate space (e.g., a coordinate space fixed relative to the wearable head device 400A) to an inertial coordinate space (e.g., a coordinate space fixed relative to the real environment), for example in order to compensate for the movement of the wearable head device 400A relative to the coordinate system 108. For instance, such transformations may be necessary for a display of the wearable head device 400A to present a virtual object at an expected position and orientation relative to the real environment (e.g., a virtual person sitting in a real chair, facing forward, regardless of the wearable head device's position and orientation), rather than at a fixed position and orientation on the display (e.g., at the same position in the right lower corner of the display), to preserve the illusion that the virtual object exists in the real environment (and does not, for example, appear positioned unnaturally in the real environment as the wearable head device 400A shifts and rotates). In some examples, a compensatory transformation between coordinate spaces can be determined by processing imagery from the depth cameras 444 using a SLAM and/or visual odometry procedure in order to determine the transformation of the wearable head device 400A relative to the coordinate system 108. In the example shown in FIG. 4, the depth cameras 444 are coupled to a SLAM/visual odometry block 406 and can provide imagery to block 406. The SLAM/visual odometry block 406 implementation can include a processor configured to process this imagery and determine a position and orientation of the user's head, which can then be used to identify a transformation between a head coordinate space and another coordinate space (e.g., an inertial coordinate space). Similarly, in some examples, an additional source of information on the user's head pose and location is obtained from an IMU 409. Information from the IMU 409 can be integrated with information from the SLAM/visual odometry block 406 to provide improved accuracy and/or more timely information on rapid adjustments of the user's head pose and position.

In some examples, the depth cameras 444 can supply 3D imagery to a hand gesture tracker 411, which may be implemented in a processor of the wearable head device 400A. The hand gesture tracker 411 can identify a user's hand gestures, for example by matching 3D imagery received from the depth cameras 444 to stored patterns representing hand gestures. Other suitable techniques of identifying a user's hand gestures will be apparent.

In some examples, one or more processors 416 may be configured to receive data from the wearable head device's 6DOF headgear subsystem 404B, the IMU 409, the SLAM/visual odometry block 406, depth cameras 444, and/or the hand gesture tracker 411. The processor 416 can also send and receive control signals from the 6DOF totem system 404A. The processor 416 may be coupled to the 6DOF totem system 404A wirelessly, such as in examples where the handheld controller 400B is untethered. Processor 416 may further communicate with additional components, such as an audio-visual content memory 418, a Graphical Processing Unit (GPU) 420, and/or a Digital Signal Processor (DSP) audio spatializer 422. The DSP audio spatializer 422 may be coupled to a Head Related Transfer Function (HRTF) memory 425. The GPU 420 can include a left channel output coupled to the left source of imagewise modulated light 424 and a right channel output coupled to the right source of imagewise modulated light 426. GPU 420 can output stereoscopic image data to the sources of imagewise modulated light 424, 426, for example as described above with respect to FIGS. 2A-2D. The DSP audio spatializer 422 can output audio to a left speaker 412 and/or a right speaker 414. The DSP audio spatializer 422 can receive input from processor 419 indicating a direction vector from a user to a virtual sound source (which may be moved by the user, e.g., via the handheld controller 320). Based on the direction vector, the DSP audio spatializer 422 can determine a corresponding HRTF (e.g., by accessing a HRTF, or by interpolating multiple HRTFs). The DSP audio spatializer 422 can then apply the determined HRTF to an audio signal, such as an audio signal corresponding to a virtual sound generated by a virtual object. This can enhance the believability and realism of the virtual sound, by incorporating the relative position and orientation of the user relative to the virtual sound in the mixed reality environment—that is, by presenting a virtual sound that matches a user's expectations of what that virtual sound would sound like if it were a real sound in a real environment.

In some examples, such as shown in FIG. 4, one or more of processor 416, GPU 420, DSP audio spatializer 422, HRTF memory 425, and audio/visual content memory 418 may be included in an auxiliary unit 400C (which may correspond to auxiliary unit 320 described above). The auxiliary unit 400C may include a battery 427 to power its components and/or to supply power to the wearable head device 400A or handheld controller 400B. Including such components in an auxiliary unit, which can be mounted to a user's waist, can limit the size and weight of the wearable head device 400A, which can in turn reduce fatigue of a user's head and neck.

While FIG. 4 presents elements corresponding to various components of an example mixed reality system, various other suitable arrangements of these components will become apparent to those skilled in the art. For example, elements presented in FIG. 4 as being associated with auxiliary unit 400C could instead be associated with the wearable head device 400A or handheld controller 400B. Furthermore, some mixed reality systems may forgo entirely a handheld controller 400B or auxiliary unit 400C. Such changes and modifications are to be understood as being included within the scope of the disclosed examples.

Delayed Audio Following

MR systems can be well-positioned to utilize sensing and/or computing to provide an immersive audio experience. In particular, MR systems can offer unique ways of spatializing sound to immerse a user in a MRE. MR systems can include speakers for presenting audio signals to users, such as described above with respect to speakers 412 and 414. An MR system can determine an audio signal to play based on a virtual environment (e.g., a MRE); for example, an audio signal can adopt certain characteristics depending on a location in the virtual environment (e.g., an origin of a sound in the virtual environment), and the user's location in the virtual environment. Similarly, audio signals can adopt audio characteristics that simulate the effect of a sound traveling at a velocity, or with an orientation, in the virtual environment. These characteristics can include placement in a stereo field. Some audio systems (e.g., headphones) divide a soundtrack into one or more channels to present audio as originating from different locations. For example, headphones may utilize two channels, one channel for each ear of a user. If a soundtrack accompanies a virtual object moving across a screen (e.g., a plane flying across the screen in a movie), an accompanying sound (e.g., engine noise) may be presented as moving from the user's left side to the user's right side. Because the audio simulates how a person perceives a real object moving through the real world, the spatialized audio adds to the immersion of the virtual experience.

Some audio systems may suffer limitations in their ability to provide immersive spatialized audio. For example, some headphone systems may present sound in a stereo field by separately presenting left and right audio channels to a user's left and right ears; but without knowledge of the location (e.g., position and/or orientation) of the user's head, the sound may be heard to be statically fixed in relation to the user's head. For example, a sound presented to a user's left ear through a left channel may continue to be presented to the user's left ear regardless of whether the user turns their head, moves forward, backward, side to side, etc. This static behavior may be undesirable for MR systems because it may be inconsistent with a user's expectations for how sounds dynamically behave in a real environment. For example, in a real environment with a sound source at a fixed position, a listener will expect sounds emitted by that source, and heard by the listener's left and right ears, to become louder or softer, or to exhibit other dynamic audio characteristics (e.g., Doppler effects), in accordance with how the user moves and rotates with respect to that sound source's position. For example, if a static sound source is initially located on a user's left side, the sounds emitted by that sound source may predominate in the user's left ear as compared to the user's right ear. But if the user rotates 180 degrees, such that the sound source is now located on the user's right side, the user will expect the sounds to predominate in the user's right ear. Similarly, while the user moves, the sound source may continually appear to be changing location relative to the user (e.g., minute positional changes may result in minute, but perceptible, changes in detected volume at each ear). In virtual or mixed reality environments, when sounds that behave in accordance with a user's expectations, based on real-world audio experiences, the user's sense of place and immersion can be enhanced. Additionally, users can take advantage of realistic audio cues to identify and place a sound source within the environment.

MR systems (e.g., MR system 112, 200) can enhance the immersion of spatialized audio by adapting real-world audio behavior. For example, a MR system may utilize one or more cameras of the MR system and/or one or more inertial measurement unit sensors to perform SLAM computations. Using SLAM techniques, a MR system may construct a three-dimensional map of its surroundings and/or identify a location of the MR system within the surroundings. In some embodiments, a MR system may utilize SLAM to estimate headpose, which can include information about a user's head's position (e.g., location and/or orientation) in three-dimensional space. In some embodiments, the MR system may utilize one or more coordinate frames to identify locations of objects and/or the MR system in an "absolute" sense (e.g., a virtual object's location may be tied to a real location of a real environment instead of simply being locked relative to the MR system or a screen).

FIG. 5 illustrates an example of mixed reality spatialized audio, according to some embodiments. In some embodiments, a MR system may use SLAM techniques to place one or more virtual objects 504a and 504b in a MRE such that the virtual objects are fixed relative to the environment, instead of fixed relative to a user. In some embodiments, virtual objects 504a and 504b can be configured to be sources of sound. Virtual objects 504a and/or 504b may be visible (e.g., as a virtual guitar) to user 502, or virtual objects 504a and/or 504b may not be visible to a user (e.g., as invisible points from which sound radiates). Using SLAM techniques, a MR system can place multiple virtual sound sources (e.g., virtual objects 504a and/or 504b) around user 502 to present spatialized audio. As user 502 rotates their head, user 502 may be able to perceive the location of virtual objects 504a and 504b (e.g., by observing that virtual object 504a is louder when user 502 is in a first orientation and softer when user 502 is in a second orientation). This approach can have the advantage of allowing user 502 to perceive dynamic changes in spatialization based on movements of user 502. This may create a more immersive audio experience than fixed sounds that do not adapt to a location of user 502.

However, in some embodiments, the exemplary approach shown in FIG. 5 may suffer from some disadvantages. In some applications, such as composed music scores, a sound designer may wish to limit the degree to which a sound exhibits spatialized behavior. Further, in some situations, spatialized audio may lead to harsh or unpleasant results. For example, fixing virtual object 504b relative to position in a MRE may mean that a sound radiating from virtual object 504b can become louder than intended when user 502 approaches virtual object 504b. If virtual object 504b corresponds to the sound of a cello and is part of a virtual orchestra, the orchestral sound may sound distorted to user 502 if user 502 is standing too close to virtual object 504b. It may not be desirable to allow a user (e.g., user 502) to walk too close to a sound source (e.g., virtual object 504b) because it may deviate from a designed experience. For example, the overpowering sound of a virtual cello may drown out sounds from virtual violins.

In addition to possibly deviating from a designed experience, allowing a user to approach a virtual sound source may be confusing or disconcerting to the user—particularly in extreme examples, such as where a user's location very nearly overlaps with the location of a sound source, or where a user's head moves or rotates at high speeds with respect to the sound source. In some embodiments, virtual object 504b may be an invisible point from which sound radiates. If user 502 approaches virtual object 504b, user 502 may perceive sound to be distinctly radiating from an invisible point. This can be undesirable if, for example, the sound draws unwanted attention to virtual object 504b (e.g., if virtual object 504b was configured to be invisible to avoid attracting the user's attention). In some embodiments, an intended central focus for a user may be visuals and/or a narrative story, and spatialized audio may be used to enhance the user's immersion in the visuals and/or narrative story. For example, a MR system may present a three-dimensional "movie" to a user where the user may walk around and observe characters and/or objects from different perspectives. In such applications, it can be disconcerting for a user to perceive an invisible point located in the mixed reality scene where sound is radiating from. For example, in a battle scene, it may not be desirable to allow a user to approach a point where an invisible guitar track is playing from. Sound designers and story creators may wish to obtain additional control over a spatialized audio experience, in order to preserve the intended narrative. It can therefore be desirable to develop additional methods of providing immersive, spatialized audio. For example, it can be desirable to permit audio designers to create custom audio behaviors (e.g., controlled by scripts executed by a scripting engine) that can be associated with sounds on an individual basis. In some cases, default audio behaviors can apply unless overridden by a custom audio behavior. In some cases, custom audio behaviors can include manipulating a sound's origin in order to produce a desired audio experience.

Figure 6A:
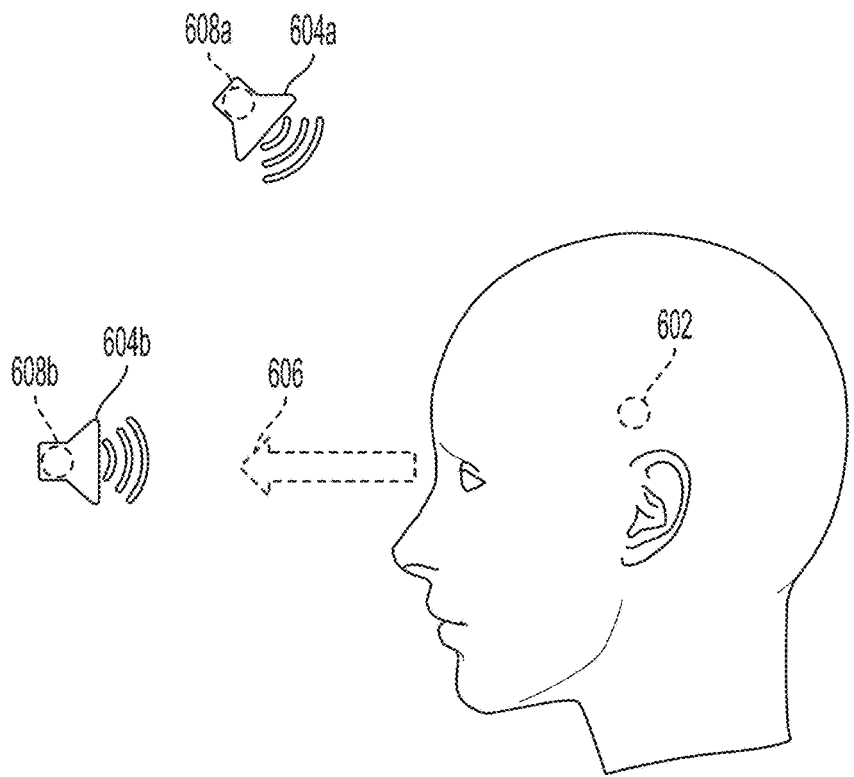
FIGS. 6A-6C illustrate examples of mixed reality spatialized audio, according to some embodiments.
Figure 6B:
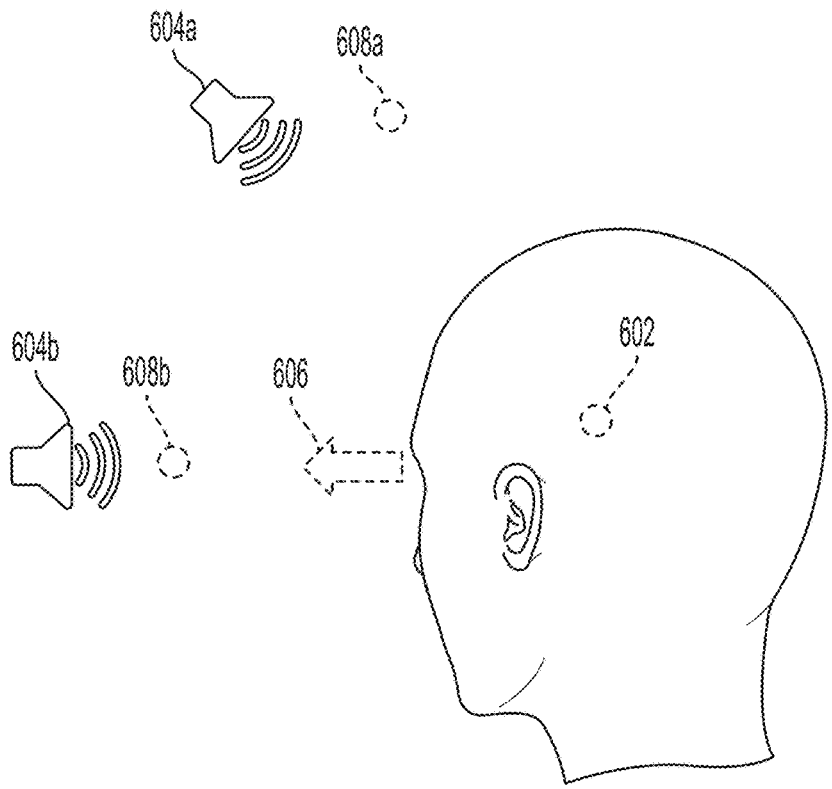
Figure 6C:
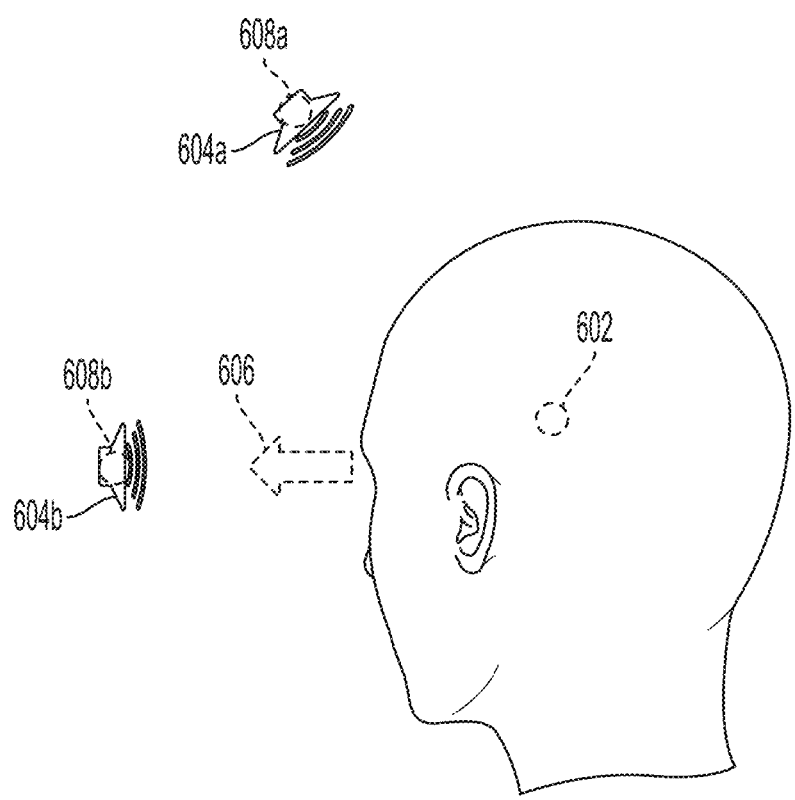

FIGS. 6A-6C illustrate examples of mixed reality spatialized audio, according to some embodiments. Spatialized audio can create a plausible three-dimensional MRE (e.g., MRE 150) experience in a similar manner as persistent visual content. As a user walks around a real environment (e.g., real environment 100), the user may expect to see persistent virtual content behave like real objects (e.g., the persistent virtual content appears larger as a user approaches it and gets smaller as the user moves away). Similarly, a user may expect sound sources to behave as if the sound sources existed in a real environment while the user moves around (e.g., a sound source may sound louder as a user approaches it and may sound softer as the user moves away). In some embodiments, immersive, spatialized audio can be controlled by manipulating a sound source with respect to a user's head—for instance, through a "delayed follow" effect. For example, one or more sound sources can be spaced around and/or tied to a user's head in a first position. At the first position, the one or more sound sources may be located at designated positions, which may be positions intended (e.g., by a developer or audio designer) for sound sources to produce a particular audio experience. A sound source's position can correspond to an origin of the sound source—e.g., a coordinate in a MRE from which the sound appears to originate. A sound source origin can be expressed as an offset (e.g., a vector offset) from a user's head (or other listener position); that is, presenting a sound to a user can comprise determining an offset from a user's head, and applying that offset to the user's head to arrive at the sound source origin. A first position of the user's head at a first time can be determined, for example by one or more sensors of a wearable head device, such as described above (e.g., with respect to wearable head device 401A). A second position of the user's head at a second, later time can then be determined. Differences between the first and second positions of the head can be used to manipulate an audio signal. For example, in some cases, when the user moves their head to the second position, the one or more sound sources can be instructed to "trail" the movement of the head such that the position of sound sources may deviate from their designated positions, which may be spaced around and/or tied to the user's head (e.g., the designated positions spaced around and/or tied to the user's head may move/change in relation to the user's head, and the sound sources may no longer be located at their designated positions spaced around and/or tied to the user's head). This manipulation of the sound source can be implemented, for example, by moving the sound source origin from a first position, by an amount less than a difference between the first and second positions of the head. In some embodiments, designated positions may remain fixed relative to a user's head position, but corresponding virtual sound sources may be "elastically" tied to the user's head position, and may trail behind a corresponding designated position. In some embodiments, the sound sources may return to their designated positions spaced around and/or tied to the user's head (e.g., the same positions intended to produce the particular audio experience) at some point after the user's head has reached the second position. Other manipulations of the sound source origin, such as others that determine the origin based on a difference between first and second head positions, are contemplated and are within the scope of this disclosure. More generally, custom audio dynamics can be created by manipulating the origin of a sound source with respect to the user's head, or to some other object (including a moving object) in a MRE. For instance, the sound source origin can be defined as a function of a user's head position and orientation, or functions of the change or accumulation of the head position or orientation over time (e.g., functions of integrals or derivatives of the head position or orientation). Such functions can be used for creative effect, such as to simulate a sound traveling at a particular velocity, or in a particular direction. For instance, a velocity of a user's head movement can be determined (e.g., as the derivative of the head movement, determined by one or more sensors of a wearable head device as described above), and a sound can be presented as if the sound origin is traveling at that same velocity (or a different velocity based on the head's velocity). As another example, a change in orientation of a user's head can be determined, such as via one or more sensors of a wearable head device such as described above, and a sound can be presented as if the sound origin is moving with an orientation based on the change in the user's head orientation. Expressing a sound origin as a function of the user's head position or orientation can also be adapted to gracefully handle situations that would otherwise cause undesirable audio results. For example, by defining a function that limits the degree to which sound sources move relative to a user's head, extreme or unwanted audio effects from those sound sources can be limited or avoided. This can be implemented, for instance, by establishing a threshold rate of change of the user's head position; if the rate of change exceeds the threshold, the change in position of a sound source origin can be limited accordingly (e.g., by setting the origin to a first coordinate if the threshold is exceeded, and setting the origin to a different coordinate if the threshold is not exceeded). As another example of avoiding unwanted audio effects, a sound source origin can be configured to always remain at least a minimum distance from the user; for instance, if the magnitude of an offset between the sound source origin and the user's head falls below a minimum threshold, the origin can be relocated to an alternate position that is at least a minimum distance from the user's head.

As shown in FIG. 6A, in some embodiments, virtual objects 604a and/or 604b may be spaced around and/or tied to center 602. Virtual objects 604a and/or 604b may be visible (e.g., displayed to a user) or invisible (e.g., not displayed to a user). In some embodiments, virtual objects 604a and/or 604b may not interact with other virtual objects. For example, virtual objects 604a and/or 604b may not collide with other virtual objects; virtual objects 604a and/or 604b may not reflect/absorb/transmit light from other virtual objects; and/or virtual objects 604a and/or 604b may not reflect/absorb/transmit sound from other virtual objects. In some embodiments, virtual objects 604a and/or 604b may interact with other virtual objects.

In some embodiments, virtual objects 604a and/or 604b may be associated with one or more sound sources. In some cases, each virtual object may correspond to one sound source. For example, virtual objects 604a and/or 604b may be configured to virtually radiate sound from their locations in a MRE. Configuring a sound source so that it can be perceived as radiating from a certain location can be done using any suitable method. For example, a head-related transfer function ("HRTF") can be used to simulate a sound originating from a particular location. In some embodiments, a generic HRTF can be used. In some embodiments, one or more microphones, for example, around a user's ear (e.g., one or more microphones of a MR system) can be used to determine one or more user-specific HRTFs. In some embodiments, a distance between a user and a virtual sound source may be simulated using suitable methods (e.g., loudness attenuation, high frequency attenuation, a mix of direct and reverberant sounds, motion parallax, etc.). In some embodiments, virtual objects 604a and/or 604b may be configured to radiate sound as a point source. In some embodiments, virtual objects 604a and/or 604b may include a physical three-dimensional model of a sound source, and a sound may be generated by modelling interactions with the sound source. For example, virtual object 604a may include a virtual guitar including a wood body, strings, tuning pegs, etc. A sound may be generated by modelling plucking one or more strings and how the action interacts with other components of the virtual guitar.

In some embodiments, virtual objects 604a and/or 604b may radiate sound omnidirectionally. In some embodiments, virtual objects 604a and/or 604b may radiate sound directionally. In some embodiments, virtual objects 604a and/or 604b may be configured to include sound sources, where each sound source may include a music stem. In some embodiments, a music stem may be an arbitrary subset of an entire musical sound. For example, an orchestral soundtrack may include a violin stem, a cello stem, a bass stem, a trumpet stem, a timpani stem, etc. In some embodiments, channels of a multi-channel sound track can be represented as stems. For example, a two-channel sound track may include a left stem and a right stem. In some embodiments, single tracks of a mix may be represented as stems. In some embodiments, a musical soundtrack may be split into stems according to frequency bands. Stems can represent any arbitrary subset of an entire sound.

In some embodiments, virtual objects 604a and/or 604b may be tied to one or more objects (e.g., center 602 and/or vector 606). For example, virtual object 604a may be assigned to designated position 608a. In some embodiments, designated position 608a can be a fixed point relative to vector 606 and/or center 602. In some embodiments, virtual object 604b may be assigned to designated position 608b. In some embodiments, designated position 608b can be a fixed point relative to vector 606 and/or center 602. Center 602 can be a point and/or a three-dimensional object. In some embodiments, virtual objects 604a and/or 604b may be tied to a point of a three-dimensional object (e.g., a center point, or a point on a surface of the three-dimensional object). In some embodiments, center 602 can correspond to any suitable point (e.g., a center of a user's head). A center of a user's head may be estimated using a center of a head-wearable MR system (which may have known dimensions) and average head dimensions, or using other suitable methods. In some embodiments, virtual objects 604a and/or 604b may be tied to a directional indicator (e.g., vector 606). In some embodiments, virtual objects 604a and/or 604b can be placed in a designated position, which may include and/or be defined by its position relative to center 602 and/or vector 606 (e.g., using a spherical coordinate system). In some embodiments, virtual objects 604a and/or 604b may deviate from their designated positions if center 602 and/or vector 606 changes position (e.g., location and/or orientation). In some embodiments, virtual objects 604a and/or 604b may return to their designated positions after center 602 and/or vector 606 stops changing position, for example after center 602 and/or vector 606 has a fixed position/value for a predetermined period of time (e.g., 5 seconds).

As shown in FIG. 6B, vector 606 may change direction. In some embodiments, designated positions 608a and/or 608b may move correspondingly. For example, designated positions 608a and/or 608b may be in the same position relative to center 602 and/or vector 606 in FIG. 6B as they are in FIG. 6A. In some embodiments, virtual objects 604a and/or 604b may trail a movement of designated positions 608a and/or 608b. For example, as vector 606 moves from a first position in FIG. 6A to a second position in FIG. 6B (e.g., to reflect a rotation of a user's head), virtual objects 604a and/or 604b may remain in the same position in both FIG. 6A and FIG. 6B (even as designated positions 608a and/or 608b move). In some embodiments, virtual objects 604a and/or 604b may begin moving after vector 606 and/or center 602 has moved and/or begun moving. In some embodiments, virtual objects 604a and/or 604b may begin moving after vector 606 and/or center 602 has stopped moving, for example for a predetermined period of time. In FIG. 6C, virtual objects 604a and/or 604b may return to their designated positions relative to vector 606 and/or center 602. For example, virtual objects 604a and/or 604b may occupy the same positions relative to vector 606 and/or center 602 in FIG. 6C as they do in FIG. 6A.

Virtual objects 604a and/or 604b may deviate from their designated positions 608a and/or 608b for a period of time. In some embodiments, as vector 606 and/or center 602 changes direction, virtual objects 604a and/or 604b may "trace" the movement path of designated position 608a and/or 608b, respectively. In some embodiments, virtual objects 604a and/or 604b may follow an interpolated path from their current position to designated position 608a and/or 608b, respectively. In some embodiments, virtual objects 604a and/or 604b may return to their designated positions once center 602 and/or vector 606 stop accelerating and/or moving altogether (e.g., linear and/or angular acceleration). For example, center 602 may remain a stationary point and vector 606 may rotate about center 602 (e.g., because a user is rotating their head) at a constant velocity. After a period of time, virtual objects 604a and/or 604b may return to their designated positions despite the fact that vector 606 remains moving at a constant velocity. Similarly, in some embodiments, center 602 may move at a constant velocity (and vector 606 may remain stationary or may also move in a constant velocity), and virtual objects 604a and/or 604b may return to their designated positions after the initial acceleration ceases. In some embodiments, virtual objects 604a and/or 604b may return to their designated positions once center 602 and/or vector 606 stop moving. For example, if a user's head is rotating at a constant velocity, virtual objects 604a and/or 604b may continue to "lag" behind their designated positions until the user stops spinning their head. In some embodiments, virtual objects 604a and/or 604b may return to their designated positions once center 602 and/or vector 606 stop accelerating. For example, if a user's head starts rotating and then continues rotating at a constant velocity, virtual objects 604a and/or 604b may initially lag behind their designated positions and then reach their designated positions after the user's head has reached a constant velocity (e.g., for a threshold period of time).

In some embodiments, the one or more sound sources may move as if they were "elastically" tied to the user's head. For example, as a user rotates their head from a first position to a second position, the one or more sound sources may not rotate at the same angular velocity as the user's head. In some embodiments, the one or more sound sources may begin rotating at a slower angular velocity than the user's head, accelerate angular velocity, and decelerate angular velocity as they approach their initial positions relative to the user's head. The rate of change of angular velocity may be capped, for example, at a level preset by a sound designer. This can strike a balance between allowing sound sources to move too quickly (which can result in unwanted audio effects, such as described above) and preventing sound sources from moving at all (which may not carry the benefits of spatialized audio).

In some embodiments, having one or more spatialized sound sources perform a delayed follow can have several advantages. For example, allowing a user to deviate in relative position from a spatialized sound source can allow the user to perceive a difference in the sound. A user may notice that a spatialized sound is slightly quieter as the user turns away from the spatialized sound, enhancing the user's immersion in the MRE. In some embodiments, delayed follow can also maintain a desired audio experience. For example, a user may be prevented from unintentionally distorting an audio experience by approaching a sound source and remaining very near the sound source. If a sound source is placed statically relative to an environment, the user may approach the sound source, and a spatializer may undesirably present the sound source as overpowering other sound sources as a result of the user's proximity (particularly as the distance between the user and the sound source approaches zero). In some embodiments, delayed follow may move a sound source to a set position, relative to a user, after a delay, so that the user may experience enhanced spatialization without compromising an overall audio effect (e.g., because each sound source may be generally maintained at desired distances from each other and/or from the user).

In some embodiments, virtual objects 604a and/or 604b can have dynamic designated positions. For example, designated position 608a may be configured to move (e.g., orbit a user's head or move closer and/or further away from a user's head) even if center 602 and vector 606 remain stationary. In some embodiments, a dynamic designated position can be determined in relation to a center and/or vector (e.g., a moving center and/or vector), and a virtual object can move towards its designated position in a delayed follow manner (e.g., by tracing movements of the designated position and/or interpolating a path).

In some embodiments, virtual objects 604a and/or 604b can be placed in their designated positions using an asset design tool for a game engine (e.g., Unity). In some embodiments, virtual objects 604a and/or 604b may include a game engine object, which may be placed in a three-dimensional environment (e.g., a MRE supported by a game engine). In some embodiments, virtual objects 604a and/or 604b may be components of a parent object. In some embodiments, a parent object may include parameters such as a corresponding center and/or vector for placing virtual objects in designated positions. In some embodiments, a parent object may include delayed follow parameters, such as a parameter for how quickly a virtual object should return to its designated position and/or under what circumstances (e.g., constant velocity or no motion) a virtual object should return to its designated position. In some embodiments, a parent object may include a parameter for a speed at which a virtual object chases its designated position (e.g., whether a virtual object should move at a constant velocity, accelerate, and/or decelerate). In some embodiments, a parent object may include a parameter to determine a path a virtual object may take from its current position to its designated position (e.g., using linear and/or exponential interpolation). In some embodiments, a virtual object (e.g., virtual objects 604a and 604b) may include its own such parameters.

In some embodiments, a game engine may maintain some or all properties of virtual objects 604a and 604b (e.g., a current and/or designated location of virtual objects 604a and 604b). In some embodiments, a current location of virtual objects 604a and 604b (e.g., through a location and/or properties of a parent object or a location and/or properties of virtual objects 604 and 604b directly) may be passed to a spatializing and/or rendering engine. For example, a spatializing and/or rendering engine may receive a sound emanating from virtual object 604a as well as a current position of virtual object 604a. The spatializing and/or rendering engine may process the inputs and produce an output that may include a spatialized sound that can be configured to perceive the sound as originating from the location of virtual object 604a. Spatializing and/or rendering engine may use any suitable techniques to render spatialized sound, including but not limited to head-related transfer functions and/or distance attenuation techniques.

In some embodiments, a spatializing and/or rendering engine may receive a data structure to render delayed follow spatialized sound. For example, a delayed follow data structure may include a data format with parameters and/or metadata regarding position relative to headpose and/or delayed follow parameters. In some embodiments, an application running on a MR system may send one or more delayed follow data structures to a spatializing and/or rendering engine to render delayed follow spatialized sound.

In some embodiments, a soundtrack may be processed into a delayed follow data structure. For example, a 5.1 channel soundtrack may be split into six stems, and each stem may be assigned to one or more virtual objects (e.g., virtual objects 604a and 604b). Each stem/virtual object may be placed at a preconfigured orientation for 5.1 channel surround sound (e.g., a center speaker stem may be placed directly in front of a user's face approximately 20 feet in front of the user). In some embodiments, the delayed follow data structure may then be used by the spatializing and/or rendering engine to render delayed follow spatialized sound.

In some embodiments, delayed follow spatialized sound may be rendered for more than one user. For example, a set of virtual objects configured to surround a first user may be perceptible to a second user. The second user may observe virtual objects/sound sources following the first user in a delayed manner. In some embodiments, a set of virtual objects/sound sources may be configured to surround more than one user. For example, a center point may be calculated as a center point between the first user's head and the second user's head. A vector may be calculated as an average vector between vectors representing each user's facing direction. One or more virtual objects/sound sources may be placed relative to a dynamically calculated center point and/or vector.

Although two virtual objects are shown in FIGS. 6A-6C, it is contemplated that any number of virtual objects and/or sound sources may be used. In some embodiments, each virtual object and/or sound source may have its own, separate parameters. Although a center point/object and a vector are used to position virtual objects, any appropriate coordinate system (e.g., Cartesian, spherical, etc.) may be used.

Systems, methods, and computer-readable media are disclosed. According to some examples, a system comprises: a wearable head device having a speaker and one or more sensors; and one or more processors configured to perform a method comprising: determining, based on the one or more sensors, a first position of a user's head at a first time; determining, based on the one or more sensors, a second position of the user's head at a second time later than the first time; determining, based on a difference between the first position and the second position, an audio signal; and presenting the audio signal to the user via the speaker, wherein: determining the audio signal comprises determining an origin of the audio signal in a virtual environment; presenting the audio signal to the user comprises presenting the audio signal as if originating from the determined origin; and determining the origin of the audio signal comprises applying an offset to a position of the user's head. In some examples, determining the origin of the audio signal further comprises determining the origin of the audio signal based on a rate of change of a position of the user's head. In some examples, determining the origin of the audio signal further comprises: in accordance with a determination that the rate of change exceeds a threshold, determining that the origin comprises a first origin; and in accordance with a determination that the rate of change does not exceed the threshold, determining that the origin comprises a second origin different from the first origin. In some examples, determining the origin of the audio signal further comprises: in accordance with a determination that a magnitude of the offset is below a threshold, determining that the origin comprises a first origin; and in accordance with a determination that the magnitude of the offset is not below the threshold, determining that the origin comprises a second origin different from the first origin. In some examples, determining the audio signal further comprises determining a velocity in the virtual environment; and presenting the audio signal to the user further comprises presenting the audio signal as if the origin is in motion with the determined velocity. In some examples, determining the velocity comprises determining the velocity based on a difference between the first position of the user's head and the second position of the user's head. In some examples, the offset is determined based on the first position of the user's head.

According to some examples, a method of presenting audio to a user of a wearable head device comprises: determining, based on one or more sensors of the wearable head device, a first position of the user's head at a first time; determining, based on the one or more sensors, a second position of the user's head at a second time later than the first time; determining, based on a difference between the first position and the second position, an audio signal; and presenting the audio signal to the user via a speaker of the wearable head device, wherein: determining the audio signal comprises determining an origin of the audio signal in a virtual environment; presenting the audio signal to the user comprises presenting the audio signal as if originating from the determined origin; and determining the origin of the audio signal comprises applying an offset to a position of the user's head. In some examples, determining the origin of the audio signal further comprises determining the origin of the audio signal based on a rate of change of a position of the user's head. In some examples, determining the origin of the audio signal further comprises: in accordance with a determination that the rate of change exceeds a threshold, determining that the origin comprises a first origin; and in accordance with a determination that the rate of change does not exceed the threshold, determining that the origin comprises a second origin different from the first origin. In some examples, determining the origin of the audio signal further comprises: in accordance with a determination that a magnitude of the offset is below a threshold, determining that the origin comprises a first origin; and in accordance with a determination that the magnitude of the offset is not below the threshold, determining that the origin comprises a second origin different from the first origin. In some examples, determining the audio signal further comprises determining a velocity in the virtual environment; and presenting the audio signal to the user further comprises presenting the audio signal as if the origin is in motion with the determined velocity. In some examples, determining the velocity comprises determining the velocity based on a difference between the first position of the user's head and the second position of the user's head. In some examples, the offset is determined based on the first position of the user's head.

According to some examples, a non-transitory computer-readable medium stores instructions which, when executed by one or more processors, cause the one or more processors to perform a method of presenting audio to a user of a wearable head device, the method comprising: determining, based on one or more sensors of the wearable head device, a first position of the user's head at a first time; determining, based on the one or more sensors, a second position of the user's head at a second time later than the first time; determining, based on a difference between the first position and the second position, an audio signal; and presenting the audio signal to the user via a speaker of the wearable head device, wherein: determining the audio signal comprises determining an origin of the audio signal in a virtual environment; presenting the audio signal to the user comprises presenting the audio signal as if originating from the determined origin; and determining the origin of the audio signal comprises applying an offset to a position of the user's head. In some examples, determining the origin of the audio signal further comprises determining the origin of the audio signal based on a rate of change of a position of the user's head. In some examples, determining the origin of the audio signal further comprises: in accordance with a determination that the rate of change exceeds a threshold, determining that the origin comprises a first origin; and in accordance with a determination that the rate of change does not exceed the threshold, determining that the origin comprises a second origin different from the first origin. In some examples, determining the origin of the audio signal further comprises: in accordance with a determination that a magnitude of the offset is below a threshold, determining that the origin comprises a first origin; and in accordance with a determination that the magnitude of the offset is not below the threshold, determining that the origin comprises a second origin different from the first origin. In some examples, determining the audio signal further comprises determining a velocity in the virtual environment; and presenting the audio signal to the user further comprises presenting the audio signal as if the origin is in motion with the determined velocity. In some examples, determining the velocity comprises determining the velocity based on a difference between the first position of the user's head and the second position of the user's head. In some examples, the offset is determined based on the first position of the user's head.

Although the disclosed examples have been fully described with reference to the accompanying drawings, it is to be noted that various changes and modifications will become apparent to those skilled in the art. For example, elements of one or more implementations may be combined, deleted, modified, or supplemented to form further implementations. Such changes and modifications are to be understood as being included within the scope of the disclosed examples as defined by the appended claims.

The invention claimed is:

1. A system comprising:
a wearable head device having a speaker and one or more sensors; and
one or more processors configured to perform a method comprising:
determining, based on the one or more sensors, a first position of a user's head at a first time;
determining, based on the one or more sensors, a second position of the user's head at a second time later than the first time;
determining, based on a difference between the first position and the second position, an audio signal; and
presenting the audio signal to the user via the speaker, wherein:
determining the audio signal comprises determining an origin of the audio signal in a virtual environment;
presenting the audio signal to the user comprises presenting the audio signal as if originating from the determined origin;
determining the origin of the audio signal comprises applying an offset to a position of the user's head;
determining the audio signal further comprises determining a velocity in the virtual environment; and
presenting the audio signal to the user further comprises presenting the audio signal as if the origin is in motion with the determined velocity.

2. The system of claim 1, wherein determining the origin of the audio signal further comprises determining the origin of the audio signal based on a rate of change of a position of the user's head.

3. The system of claim 2, wherein determining the origin of the audio signal further comprises:
in accordance with a determination that the rate of change exceeds a threshold, determining that the origin comprises a first origin; and
in accordance with a determination that the rate of change does not exceed the threshold, determining that the origin comprises a second origin different from the first origin.

4. The system of claim 1, wherein determining the origin of the audio signal further comprises:
in accordance with a determination that a magnitude of the offset is below a threshold, determining that the origin comprises a first origin; and in accordance with a determination that the magnitude of the offset is not below the threshold, determining that the origin comprises a second origin different from the first origin.

5. The system of claim 1, wherein the determined velocity comprises an angular velocity.

6. The system of claim 1, wherein:
determining the velocity comprises determining the velocity based on a difference between the first position of the user's head and the second position of the user's head.

7. The system of claim 1, wherein the offset is determined based on the first position of the user's head.

8. A method of presenting audio to a user of a wearable head device, the method comprising:
determining, based on one or more sensors of the wearable head device, a first position of the user's head at a first time;
determining, based on the one or more sensors, a second position of the user's head at a second time later than the first time;
determining, based on a difference between the first position and the second position, an audio signal; and
presenting the audio signal to the user via a speaker of the wearable head device,
wherein:
determining the audio signal comprises determining an origin of the audio signal in a virtual environment;
presenting the audio signal to the user comprises presenting the audio signal as if originating from the determined origin;
determining the origin of the audio signal comprises applying an offset to a position of the user's head;
determining the audio signal further comprises determining a velocity in the virtual environment; and
presenting the audio signal to the user further comprises presenting the audio signal as if the origin is in motion with the determined velocity.

9. The method of claim 8, wherein determining the origin of the audio signal further comprises determining the origin of the audio signal based on a rate of change of a position of the user's head.

10. The method of claim 9, wherein determining the origin of the audio signal further comprises:
in accordance with a determination that the rate of change exceeds a threshold, determining that the origin comprises a first origin; and
in accordance with a determination that the rate of change does not exceed the threshold, determining that the origin comprises a second origin different from the first origin.

11. The method of claim 8, wherein determining the origin of the audio signal further comprises:
in accordance with a determination that a magnitude of the offset is below a threshold, determining that the origin comprises a first origin; and
in accordance with a determination that the magnitude of the offset is not below the threshold, determining that the origin comprises a second origin different from the first origin.

12. The method of claim 8, wherein the determined velocity comprises an angular velocity.

13. The method of claim 8, wherein:
determining the velocity comprises determining the velocity based on a difference between the first position of the user's head and the second position of the user's head.

14. The method of claim 8, wherein the offset is determined based on the first position of the user's head.

15. A non-transitory computer-readable medium storing instructions which, when executed by one or more processors, cause the one or more processors to perform a method of presenting audio to a user of a wearable head device, the method comprising:
determining, based on one or more sensors of the wearable head device, a first position of the user's head at a first time;
determining, based on the one or more sensors, a second position of the user's head at a second time later than the first time;
determining, based on a difference between the first position and the second position, an audio signal; and
presenting the audio signal to the user via a speaker of the wearable head device,
wherein:
determining the audio signal comprises determining an origin of the audio signal in a virtual environment;
presenting the audio signal to the user comprises presenting the audio signal as if originating from the determined origin;
determining the origin of the audio signal comprises applying an offset to a position of the user's head;
determining the audio signal further comprises determining a velocity in the virtual environment; and
presenting the audio signal to the user further comprises presenting the audio signal as if the origin is in motion with the determined velocity.

16. The non-transitory computer-readable medium of claim 15, wherein determining the origin of the audio signal further comprises determining the origin of the audio signal based on a rate of change of a position of the user's head.

17. The non-transitory computer-readable medium of claim 16, wherein determining the origin of the audio signal further comprises:
in accordance with a determination that the rate of change exceeds a threshold, determining that the origin comprises a first origin; and
in accordance with a determination that the rate of change does not exceed the threshold, determining that the origin comprises a second origin different from the first origin.

18. The non-transitory computer-readable medium of claim 15, wherein determining the origin of the audio signal further comprises:
in accordance with a determination that a magnitude of the offset is below a threshold, determining that the origin comprises a first origin; and
in accordance with a determination that the magnitude of the offset is not below the threshold, determining that the origin comprises a second origin different from the first origin.

19. The non-transitory computer-readable medium of claim 15, wherein the determined velocity comprises an angular velocity.

20. The non-transitory computer-readable medium of claim 15, wherein:
determining the velocity comprises determining the velocity based on a difference between the first position of the user's head and the second position of the user's head.

* * * * *

UNITED STATES PATENT AND TRADEMARK OFFICE
CERTIFICATE OF CORRECTION

PATENT NO. : 11,477,599 B2
APPLICATION NO. : 17/175269
DATED : October 18, 2022
INVENTOR(S) : Anastasia Andreyevna Tajik Page 1 of 1

It is certified that error appears in the above-identified patent and that said Letters Patent is hereby corrected as shown below:

On the Title Page

At Related U.S. Application Data (Item (60)), replace "62/976,936" with --62/976,986--.

Signed and Sealed this
Twenty-fourth Day of January, 2023

Katherine Kelly Vidal
*Director of the United States Patent and Trademark Office*